United States Patent
Evdokimov et al.

(10) Patent No.: US 11,198,886 B2
(45) Date of Patent: Dec. 14, 2021

(54) METHODS AND COMPOSITIONS FOR PPO HERBICIDE TOLERANCE IN PLANTS

(71) Applicant: Monsanto Technology LLC, St. Louis, MO (US)

(72) Inventors: Artem G. Evdokimov, Orchard Park, NY (US); Clayton T. Larue, Chesterfield, MO (US); Farhad Moshiri, Chesterfield, MO (US); Joel E. Ream, St. Louis, MO (US); Xuefeng Zhou, St. Louis, MO (US)

(73) Assignee: Monsanto Technology LLC, St. Louis, MO (US)

(*) Notice: Subject to any disclaimer, the term of this patent is extended or adjusted under 35 U.S.C. 154(b) by 35 days.

(21) Appl. No.: 16/452,327

(22) Filed: Jun. 25, 2019

(65) Prior Publication Data

US 2019/0382787 A1 Dec. 19, 2019

Related U.S. Application Data

(62) Division of application No. 15/224,276, filed on Jul. 29, 2016, now Pat. No. 10,370,677.

(60) Provisional application No. 62/200,428, filed on Aug. 3, 2015.

(51) Int. Cl.
| | |
|---|---|
| *C12N 15/82* | (2006.01) |
| *C12Q 1/68* | (2018.01) |
| *C12N 9/02* | (2006.01) |
| *C12Q 1/32* | (2006.01) |

(52) U.S. Cl.
CPC ......... *C12N 15/8274* (2013.01); *C12N 9/001* (2013.01); *C12Q 1/32* (2013.01); *C12Y 103/03004* (2013.01); *G01N 2333/90206* (2013.01); *G01N 2430/20* (2013.01)

(58) Field of Classification Search
None
See application file for complete search history.

(56) References Cited

U.S. PATENT DOCUMENTS

| | | | |
|---|---|---|---|
| 6,905,852 B1 * | 6/2005 | Horikoshi | C12N 9/001 435/189 |
| 11,124,803 B2 | 9/2021 | LaRue et al. | |
| 2003/0233675 A1 | 12/2003 | Cao et al. | |
| 2007/0050863 A1 | 3/2007 | Tranel et al. | |
| 2014/0123340 A1 * | 5/2014 | Aponte | C12Y 103/03004 800/278 |
| 2017/0058290 A1 | 3/2017 | Evdokimov et al. | |
| 2017/0175131 A1 | 6/2017 | Ellis et al. | |
| 2018/0044690 A1 | 2/2018 | Larue et al. | |
| 2019/0185873 A1 | 6/2019 | Larue et al. | |

FOREIGN PATENT DOCUMENTS

| | | |
|---|---|---|
| WO | WO 95/34659 | 6/1995 |
| WO | WO/1997/041228 | 11/1997 |
| WO | WO 98/33927 | 1/1998 |
| WO | 2015027258 A2 | 3/2015 |
| WO | 2015092706 | 6/2015 |
| WO | 2016203377 A1 | 12/2016 |
| WO | 2017198859 | 11/2017 |
| WO | 2018022777 | 2/2018 |

OTHER PUBLICATIONS

Pectobacterium polaris menaquinone-dependent protoporphyrinogen IX dehydrogenase, UniProtKB Accession No. A0A093V7L1, published Nov. 26, 2014.*
*Pectobacterium carotovorum* subsp. *carotovorum* (strain PC1) protoporphyrinogen oxidase, UniProtKB Accession No. C6DHI2, published Sep. 1, 2009.*
Hao et al., 2011, Protoporphyrinogen oxidase inhibitor: an ideal target for herbicide discovery, CHIMIA 65: 961-969.*
Keskin et al., 2004, A new, structurally nonredundant, diverse data set of protein-protein interfaces and its implications, Protein Science 13: 1043-1055.*
Guo et al., 2004, Protein tolerance to random amino acid change, Proceedings of the National Academy of Sciences USA 101: 9205-9210.*
Thornton et al., 2000, From structure to function: approaches and limitations, Nature Structural Biology, structural genomic supplement, Nov. 2000: 991-994.*
GenBank Accession No. CP001699, dated Dec. 24, 2013.
UniProtKB Accession No. C7PKZ1, dated Oct. 13, 2009.
USPTO: Notice of Allowance and Fee(s) Due regarding U.S. Appl. No. 15/660,660, dated Apr. 14, 2020.
Nishimura et al., "Cloning and Identification of the hemG Gene Encoding Protoporphyrinogen Oxidase (PPO) of *Escherichia coli* K-12", DNA Research 2 (1):1-8 (1995).
Supplementary European Search Report regarding Europe Patent Application No. 16842539, dated Aug. 7, 2019.
EBI Accession No. ACU63901 dated Aug. 21, 2009.
U.S. Appl. No. 16/931,427, filed Jul. 16, 2020, Larue et al.
U.S. Appl. No. 16/218,822, filed Dec. 13, 2018, Larue et al.
Becker et al., "The cab-m7 gene: a light-inducible, mesophyll-specific gene of maize," Plant Mol Biol, 20:49-60, 1992.
Boynton et al., "Discovery of a gene involved in a third bacterial protoporphyrinogen oxidase activity through comparative genomic analysis and functional complementation," *Appl Environ Microbiol*, 77:4795-4801, 2011.

(Continued)

*Primary Examiner* — Bratislav Stankovic
(74) *Attorney, Agent, or Firm* — Dentons US LLP; Elizabeth Millard

(57) ABSTRACT

The invention relates to biotechnology and provides novel recombinant DNA molecules and engineered proteins for conferring tolerance to protoporphyrinogen oxidase-inhibitor herbicides. The invention also provides herbicide tolerant transgenic plants, seeds, cells, and plant parts containing the recombinant DNA molecules, as well as methods of using the same.

25 Claims, 2 Drawing Sheets

Specification includes a Sequence Listing.

(56) References Cited

OTHER PUBLICATIONS

Creissen et al., "Simultaneous targeting of pea glutathione reductase and of a bacterial fusion protein to chloroplasts and mitochondria," *Plant J*, 8:167-175, 1995.
della-Cioppa et al., "Translocation of the precursor of 5-enolpyruvylshikimate-3-phosphate synthase into chloroplasts of higher plants in vitro," *Proc Natl Acad Sci U S A*, 83:6873-6877, 1986.
Ecogene Accession No. EG11485.
de Castro Silva Filho et al., "Mitochondrial and chloroplast targeting sequences in tandem modify protein import specificity in plant organelles," *Plant Mol Biol*, 30:769-780, 1996.
GenBank Accession No. WP_021498199.
GenBank Accession No. ABD52326.
Grossmann et al., "The herbicide Saflufenacil (Kixor™) is a new inhibitor of protoporphyrinogen IX oxidase activity," *Weed Sci*, 58:1-9, 2010.
Hansson et al., "Cloning and characterization of the *Bacillus subitlis* hemEHY gene cluster, which encodes protoheme IX biosynthetic enzymes," *J Bacteriol*, 174:8081-8093, 1992.
Jacobs et al., "Measurement of protoporphyrinogen oxidase activity," *Curr Protoc Toxicol*, 8.5.1-8.5.13, 1999.
Klee et al., "Cloning of an *Arabidopsis thaliana* gene encoding 5-enolpyruvylshikimate-3-phosphate synthase: sequence analysis and manipulation to obtain glyphosate-tolerant plants" *Mol Gen Genet*, 210:437-442, 1987.
Matsumoto et al., Porphyrin intermediate involved in herbicidal action of delta-aminoleuvlinic acid on duckweek (*Lemna pauciostata* Hegelm.), *Pestic Biochem Physiol*, 48:214-221, 1994.
Patzoldt et al., "A codon deletion confers resistance to herbicides inhibiting protoporphyrinogen oxidase," *Proc Natl Acad Sci U S A*, 103:12329-12334, 2006.
Sasarman et al., "Mapping of a new hem gene in *Escherichia coli* K12," *J Gen Microbiol*, 113:297-303, 1979.
Sasarman et al., "Nucleotide sequence of the hemG gene involved in the protoporphyrinogen oxidase activity of *Escherichia coli* K12," *Can J Microbiol*, 39:1155-1161, 1993.
International Search Report and Written Opinion regarding International Application No. PCT/US2016/044774, dated Dec. 28, 2016.
Uniprot A0A085G3K7 Full=Oxygen-independent protoporphyrinogen IX oxidase. [online] Mar. 27, 2015 [retrieved Oct. 5, 2016]. Available on the internet: <URL: http://www.uniprot.org/uniprot/A0A085G3K7.txt?version=4>.
GenBank Accession No. CP002505, dated Jan. 7, 2015.
Boynton et al., "Identification of *Escherichia coli* HemG as a Novel, Menadione-Dependent Flavodoxin with Protoporphyrinogen Oxidase Activity," *Biochemistry* 48(29):6705-6711, 2009.
USPTO: Non-Final Office Action regarding U.S. Appl. No. 15/228,993, dated Mar. 8, 2018.
Response to Non-Final Office Action regarding U.S. Appl. No. 15/228,993, dated Jun. 6, 2018.
USPTO: Final Office Action regarding U.S. Appl. No. 15/228,993, dated Jul. 23, 2018.
Response to Final Office Action regarding U.S. Appl. No. 15/228,993, dated Dec. 5, 2018.
USPTO: Non-Final Office Action regarding U.S. Appl. No. 15/228,993, dated Feb. 27, 2019.
Response to Non-Final Office Action regarding U.S. Appl. No. 15/228,993, dated Apr. 5, 2019.
USPTO: Notice of Allowance regarding U.S. Appl. No. 15/228,993, dated May 1, 2019.
Extended European Search Report regarding Europe Application No. 16833627.9, dated May 7, 2019.
Dailey et al., "Expression of a Cloned Protoporphyrinogen Oxidase," The Journal of Biological Chemistry 269(2):813-815, 1994.
Sasarman et al., "Nucleotide Sequence of the hemG gene involved in the protoporphyrinogen oxidase activity of *Escherichia coli* K12," Canadian Journal of Microbiology 39(12):1155-1161, 1993.
Hao et al., CHIMIA 65:961-969 (2011).
Keskin et al., Protein Science 13: 1043-1055 (2004).
Guo et al., Proceedings of the National Academy of Sciences USA 101: 9205-9210 (2004).
Thornton et al., Nature Structural Biology, structural genomic supplement, Nov. 2000: 991-994.
Protoporphyrinogen oxidase with a UniProtKB Accession No. A0A095G3K7, published Oct. 29, 2014.
U.S. Appl. No. 16/452,305, filed Jun. 25, 2019, Evdokimov et al.
U.S. Appl. No. 16/452,349, filed Jun. 25, 2019, Evdokimov et al.
USPTO: Non-Final Office Action regarding U.S. Appl. No. 16/452,305, dated Apr. 6, 2021.
USPTO: Non-Final Office Action regarding U.S. Appl. No. 16/452,349, dated May 21, 2021.
Glavina Del Rio, et al., Complete genome sequence of Chitinophaga pinensis type strain (UQM 2034T), Stand Genomic Sci 2(1):87-95, 2010.
GenBank Accession No. WP_034794962, dated Jun. 20, 2019.
USPTO: Notice of Allowance regarding U.S. Appl. No. 16/218,822, dated May 14, 2021.
USPTO: Response to Non-Final Office Action regarding U.S. Appl. No. 16/452,305, filed Jun. 17, 2021.
USPTO: Final Office Action regarding U.S. Appl. No. 16/452,305, dated Jul. 14, 2021.
USPTO: Response to Non-Final Office Action regarding U.S. Appl. No. 16/452,349, filed Aug. 6, 2021.
U.S. Appl. No. 17/404,857, filed Aug. 17, 2021, LaRue et al.
USPTO: Response to Final Office Action regarding U.S. Appl. No. 16/452,305, filed Sep. 14, 2021.
USPTO: Final Office Action regarding U.S. Appl. No. 16/452,349, dated Sep. 20, 2021.
USPTO: Notice of Allowance regarding U.S. Appl. No. 16/452,305, dated Sep. 28, 2021.

* cited by examiner

```
1_PPO_H_N90    MA VYYT      HA  SYI SCMKEK-AEC   IDLTHGEHVNLTQYDQ    49
2_PPO_H_N20    ....  .F.......QK...A..DEI.GQ-QS....  IQDAKTLDWQ...R  49
3_PPO_H_N60    ....  .........RK...S..DVIRQQ-QQ...L IKEASLPDWA...R   49
4_PPO_H_N10    ..T.  .F.......RE....L..EL..LGIQA..A VHRI.EPQWEN..R    50
5_PPO_H_N30    ....  .F.S.E...RE.......NSI.E-M....F ILRV.QIDWS...R    49
6_PPO_H_N40    ....  VF.S.....R.......NTL.GT-L....V WLNANDID.S...R    49
7_PPO_H_N50    ..T.  .F.......K..RH..GVLE.QGKA.ELV..LQPGEPDWSTVEC      50
8_PPO_H_N70    ....  .F.S.....QL...S..KELEG.-QA...L ILDTIN.EW....R     49
9_PPO_H_N100   ..T.  .F.......RE..AFL..EL..QGIYA...  NRI.EIAWQE..R    50
10_PPO_H_N110  ..I.  .F.......RE..ASL..EL..QAFDV..V  HRA.NIAWEE..G    50

Consensus         .  ilf .d    ..  ... .........dv.n........w...yd.     50

1_PPO_H_N90    VLGA  YG FNAVLIKFI  RFVD  NMMPSAFFQ   T   PE   TPQ     99
2_PPO_H_N20    ...........QP.VNE.  .H.LLA.QQRV.G...S...........S.E    99
3_PPO_H_N60    ...........QP.V....C LHE.QQRT.G...S...........S.E      99
4_PPO_H_N10    .V.........YHSAFQE..  R ATR..S.....YS...V...........    100
5_PPO_H_N30    ....G..H....HPAVA...   .LHE.QQRS.G..........AD.....    99
6_PPO_H_N40    .A.........R.HEAVNQ..RR LTS.QQL.....S..............I.  99
7_PPO_H_N50    .VL........HKSFIR.  NT AQR.....G.L.T...V......QS..     100
8_PPO_H_N70    ............HPAVAE..  . QRE.QQRS.G...S...........S.E   99
9_PPO_H_N100   .V.........HPAV.R..  K IET..SL.G...S...V...A......     100
10_PPO_H_N110  .V.........HST.NS..  K QQA.KKL.G..YS...V...........    100

Consensus         .iS= r h f......gyk.h... .....ff.   .   pe x.p.      100

1_PPO_H_N90      PYVR F  LATPW PALCG F    YP Y WIDKV  Q   P           149
2_PPO_H_N20    ..A.TV...AQ .....DC.A......Y......F. ....F..........  149
3_PPO_H_N60    ..A.TQ...AH .....DC.A......Y......F. ...............  149
4_PPO_H_N10    ..S.A....MN Q.R.DR.A.I...........Y. F..K...K.S....     150
5_PPO_H_N30    ..A.M.....Q .....DC.A........T....F. ...............  149
6_PPO_H_N40    ..A.T.....N .....D..C.............F. .............I..  149
7_PPO_H_N50    ..S.T.....A. ....QR.Q............S.Y. M..R...K.A....   150
8_PPO_H_N70    ..A.TA...NQ .....DC.A..............F. I..............  149
9_PPO_H_N100   ..S.T.....N .K..A.A...............Y. F..R...K......    150
10_PPO_H_N110  ..S.T.....D .....D.SA..............N.Y. I..R...KI.....  150

Consensus         .  .  . Kf  ..sp qE ..c. l   r  x . r.  . l  .mt       150

1_PPO_H_N90    DTS  E EY  LWE  KKF  EDF K SY  KAL-        179
2_PPO_H_N20    .A........Q..QR..R...Q.PG.SY--             178
3_PPO_H_N60    .ST........Q..ST..N...Q.PG.S---            177
4_PPO_H_N10    ..R...V.......AN..REI.H.TD.PT.K            181
5_PPO_H_N30    ..........T..AR..QE..H.PG.TQ--             178
6_PPO_H_N40    .ST..I......Q..AR..Q...Q.AA.NPA-           179
7_PPO_H_N50    ..R........QS.IR..REI.Q.PGETR--            179
8_PPO_H_N70    .S.........Q..TR..QE..R.PG.TS--            179
9_PPO_H_N100   ..R...V....S..AS..REIVQ.TRSSR.-            180
10_PPO_H_N110  ..R...V....Q..TH..HEIVQ.VR.----            177

Consensus         .  v.    .g ..  ...a. ..k...              181
```

FIG.1

SEQUENCE LISTING

<160> NUMBER OF SEQ ID NOS: 63

<210> SEQ ID NO 1
<211> LENGTH: 179
<212> TYPE: PRT
<213> ORGANISM: Enterobacter cloacae

<400> SEQUENCE: 1

```
Met Lys Ala Leu Val Leu Tyr Ser Thr Arg Asp Gly Gln Thr His Ala
1               5                   10                  15

Ile Ala Ser Tyr Ile Ala Ser Cys Met Lys Glu Lys Ala Glu Cys Asp
            20                  25                  30

Val Ile Asp Leu Thr His Gly Glu His Val Asn Leu Thr Gln Tyr Asp
        35                  40                  45

Gln Val Leu Ile Gly Ala Ser Ile Arg Tyr Gly His Phe Asn Ala Val
    50                  55                  60

Leu Asp Lys Phe Ile Lys Arg Asn Val Asp Gln Leu Asn Asn Met Pro
65                  70                  75                  80

Ser Ala Phe Phe Cys Val Asn Leu Thr Ala Arg Lys Pro Glu Lys Arg
                85                  90                  95

Thr Pro Gln Thr Asn Pro Tyr Val Arg Lys Phe Leu Leu Ala Thr Pro
            100                 105                 110

Trp Gln Pro Ala Leu Cys Gly Val Phe Ala Gly Ala Leu Arg Tyr Pro
        115                 120                 125

Arg Tyr Arg Trp Ile Asp Lys Val Met Ile Gln Leu Ile Met Arg Met
    130                 135                 140

Thr Gly Gly Glu Thr Asp Thr Ser Lys Glu Val Glu Tyr Thr Asp Trp
145                 150                 155                 160

Glu Gln Val Lys Lys Phe Ala Glu Asp Phe Ala Lys Leu Ser Tyr Lys
                165                 170                 175

Lys Ala Leu
```

<210> SEQ ID NO 2
<211> LENGTH: 178
<212> TYPE: PRT
<213> ORGANISM: Pantoea ananatis

<400> SEQUENCE: 2

```
Met Lys Ala Leu Ile Leu Phe Ser Thr Arg Asp Gly Gln Thr Gln Lys
1               5                   10                  15

Ile Ala Ser Ala Ile Ala Asp Glu Ile Lys Gly Gln Gln Ser Cys Asp
            20                  25                  30

Val Ile Asn Ile Gln Asp Ala Lys Thr Leu Asp Trp Gln Gln Tyr Asp
        35                  40                  45

Arg Val Leu Ile Gly Ala Ser Ile Arg Tyr Gly His Phe Gln Pro Val
    50                  55                  60

Val Asn Glu Phe Val Lys His Asn Leu Leu Ala Leu Gln Gln Arg Val
65                  70                  75                  80

Ser Gly Phe Phe Ser Val Asn Leu Thr Ala Arg Lys Pro Glu Lys Arg
                85                  90                  95

Ser Pro Glu Thr Asn Ala Tyr Thr Val Lys Phe Leu Ala Gln Ser Pro
            100                 105                 110

Trp Gln Pro Asp Cys Cys Ala Val Phe Ala Gly Ala Leu Tyr Tyr Pro
        115                 120                 125

Arg Tyr Arg Trp Phe Asp Arg Val Met Ile Gln Phe Ile Met Arg Met
    130                 135                 140

Thr Gly Gly Glu Thr Asp Ala Ser Lys Glu Val Glu Tyr Thr Asp Trp
145                 150                 155                 160

Gln Gln Val Gln Arg Phe Ala Arg Asp Phe Ala Gln Leu Pro Gly Lys
                165                 170                 175
```

Ser Tyr

<210> SEQ ID NO 3
<211> LENGTH: 177
<212> TYPE: PRT
<213> ORGANISM: Pantoea stewardii

<400> SEQUENCE: 3

```
Met Lys Ala Leu Ile Leu Tyr Ser Thr Arg Asp Gly Gln Thr Arg Lys
1               5                   10                  15

Ile Ala Ser Ser Ile Ala Asp Val Ile Arg Gln Gln Gln Cys Asp
                20                  25                  30

Val Leu Asn Ile Lys Asp Ala Ser Leu Pro Asp Trp Ala Gln Tyr Asp
            35                  40                  45

Arg Val Leu Ile Gly Ala Ser Ile Arg Tyr Gly His Phe Gln Pro Val
        50                  55                  60

Val Asp Lys Phe Val Lys Gln His Leu His Glu Leu Gln Gln Arg Thr
65                  70                  75                  80

Ser Gly Phe Phe Ser Val Asn Leu Thr Ala Arg Lys Pro Glu Lys Arg
                85                  90                  95

Ser Pro Glu Thr Asn Ala Tyr Thr Gln Lys Phe Leu Ala His Ser Pro
            100                 105                 110

Trp Gln Pro Asp Cys Cys Ala Val Phe Ala Gly Ala Leu Tyr Tyr Pro
        115                 120                 125

Arg Tyr Arg Trp Phe Asp Arg Val Met Ile Gln Leu Ile Met Arg Met
    130                 135                 140

Thr Gly Gly Glu Thr Asp Ser Thr Lys Glu Val Glu Tyr Thr Asp Trp
145                 150                 155                 160

Gln Gln Val Ser Thr Phe Ala Asn Asp Phe Ala Gln Leu Pro Gly Lys
                165                 170                 175

Ser
```

<210> SEQ ID NO 4
<211> LENGTH: 181
<212> TYPE: PRT
<213> ORGANISM: Escherichia coli

<400> SEQUENCE: 4

```
Met Lys Thr Leu Ile Leu Phe Ser Thr Arg Asp Gly Gln Thr Arg Glu
1               5                   10                  15

Ile Ala Ser Tyr Leu Ala Ser Glu Leu Lys Glu Leu Gly Ile Gln Ala
                20                  25                  30

Asp Val Ala Asn Val His Arg Ile Glu Glu Pro Gln Trp Glu Asn Tyr
            35                  40                  45

Asp Arg Val Val Ile Gly Ala Ser Ile Arg Tyr Gly His Tyr His Ser
        50                  55                  60

Ala Phe Gln Glu Phe Val Lys Lys His Ala Thr Arg Leu Asn Ser Met
65                  70                  75                  80

Pro Ser Ala Phe Tyr Ser Val Asn Leu Val Ala Arg Lys Pro Glu Lys
                85                  90                  95

Arg Thr Pro Gln Thr Asn Ser Tyr Ala Arg Lys Phe Leu Met Asn Ser
            100                 105                 110

Gln Trp Arg Pro Asp Arg Cys Ala Val Ile Ala Gly Ala Leu Arg Tyr
        115                 120                 125

Pro Arg Tyr Arg Trp Tyr Asp Arg Phe Met Ile Lys Leu Ile Met Lys
    130                 135                 140
```

```
Met Ser Gly Gly Glu Thr Asp Thr Arg Lys Glu Val Val Tyr Thr Asp
145                 150                 155                 160

Trp Glu Gln Val Ala Asn Phe Ala Arg Glu Ile Ala His Leu Thr Asp
                165                 170                 175

Lys Pro Thr Leu Lys
            180

<210> SEQ ID NO 5
<211> LENGTH: 178
<212> TYPE: PRT
<213> ORGANISM: Erwinia toletana

<400> SEQUENCE: 5

Met Lys Ala Leu Ile Leu Phe Ser Ser Arg Glu Gly Gln Thr Arg Glu
1               5                   10                  15

Ile Ala Ser Tyr Ile Ala Asn Ser Ile Lys Glu Glu Met Glu Cys Asp
                20                  25                  30

Val Phe Asn Ile Leu Arg Val Glu Gln Ile Asp Trp Ser Gln Tyr Asp
            35                  40                  45

Arg Val Leu Ile Gly Gly Ser Ile His Tyr Gly His Phe His Pro Ala
    50                  55                  60

Val Ala Lys Phe Val Lys Arg His Leu His Glu Leu Gln Gln Arg Ser
65                  70                  75                  80

Ser Gly Phe Phe Cys Val Asn Leu Thr Ala Arg Lys Ala Asp Lys Arg
                85                  90                  95

Thr Pro Gln Thr Asn Ala Tyr Met Arg Lys Phe Leu Leu Gln Ser Pro
            100                 105                 110

Trp Gln Pro Asp Cys Cys Ala Val Phe Ala Gly Ala Leu Arg Tyr Thr
        115                 120                 125

Arg Tyr Arg Trp Phe Asp Arg Val Met Ile Gln Leu Ile Met Arg Met
130                 135                 140

Thr Gly Gly Glu Thr Asp Thr Ser Lys Glu Val Glu Tyr Thr Asp Trp
145                 150                 155                 160

Thr Gln Val Ala Arg Phe Ala Gln Glu Phe Ala His Leu Pro Gly Lys
                165                 170                 175

Thr Gln

<210> SEQ ID NO 6
<211> LENGTH: 179
<212> TYPE: PRT
<213> ORGANISM: Pectobacterium carotovorum

<400> SEQUENCE: 6

Met Lys Ala Leu Ile Val Phe Ser Ser Arg Asp Gly Gln Thr Arg Ala
1               5                   10                  15

Ile Ala Ser Tyr Ile Ala Asn Thr Leu Lys Gly Thr Leu Glu Cys Asp
                20                  25                  30

Val Val Asn Val Leu Asn Ala Asn Asp Ile Asp Leu Ser Gln Tyr Asp
            35                  40                  45

Arg Val Ala Ile Gly Ala Ser Ile Arg Tyr Gly Arg Phe His Pro Ala
    50                  55                  60

Val Asn Gln Phe Ile Arg Lys His Leu Thr Ser Leu Gln Gln Leu Pro
65                  70                  75                  80

Ser Ala Phe Phe Ser Val Asn Leu Thr Ala Arg Lys Pro Glu Lys Arg
                85                  90                  95
```

```
Thr Ile Gln Thr Asn Ala Tyr Thr Arg Lys Phe Leu Leu Asn Ser Pro
                100                 105                 110

Trp Gln Pro Asp Leu Cys Cys Val Phe Ala Gly Ala Leu Arg Tyr Pro
            115                 120                 125

Arg Tyr Arg Trp Phe Asp Arg Val Met Ile Gln Leu Ile Met Arg Ile
        130                 135                 140

Thr Gly Gly Glu Thr Asp Ser Thr Lys Glu Ile Glu Tyr Thr Asp Trp
145                 150                 155                 160

Gln Gln Val Ala Arg Phe Ala Gln Asp Phe Ala Gln Leu Ala Ala Lys
                165                 170                 175

Asn Pro Ala

<210> SEQ ID NO 7
<211> LENGTH: 179
<212> TYPE: PRT
<213> ORGANISM: Shimwellia blattae

<400> SEQUENCE: 7

Met Lys Thr Leu Ile Leu Phe Ser Thr Arg Asp Gly Gln Thr His Lys
1               5                   10                  15

Ile Ala Arg His Ile Ala Gly Val Leu Glu Glu Gln Gly Lys Ala Cys
                20                  25                  30

Glu Leu Val Asp Leu Leu Gln Pro Gly Glu Pro Asp Trp Ser Thr Val
            35                  40                  45

Glu Cys Val Val Leu Gly Ala Ser Ile Arg Tyr Gly His Phe His Lys
        50                  55                  60

Ser Phe Ile Arg Phe Val Asn Thr His Ala Gln Arg Leu Asn Asn Met
65                  70                  75                  80

Pro Gly Ala Leu Phe Thr Val Asn Leu Val Ala Arg Lys Pro Glu Lys
                85                  90                  95

Gln Ser Pro Gln Thr Asn Ser Tyr Thr Arg Lys Phe Leu Ala Ala Ser
                100                 105                 110

Pro Trp Gln Pro Gln Arg Cys Gln Val Phe Ala Gly Ala Leu Arg Tyr
            115                 120                 125

Pro Arg Tyr Ser Trp Tyr Asp Arg Met Met Ile Arg Leu Ile Met Lys
        130                 135                 140

Met Ala Gly Gly Glu Thr Asp Thr Arg Lys Glu Val Glu Tyr Thr Asp
145                 150                 155                 160

Trp Gln Ser Val Thr Arg Phe Ala Arg Glu Ile Ala Gln Leu Pro Gly
                165                 170                 175

Glu Thr Arg

<210> SEQ ID NO 8
<211> LENGTH: 178
<212> TYPE: PRT
<213> ORGANISM: Pantoea stewardii

<400> SEQUENCE: 8

Met Lys Ala Leu Ile Leu Phe Ser Ser Arg Asp Gly Gln Thr Gln Leu
1               5                   10                  15

Ile Ala Ser Ser Ile Ala Lys Glu Leu Glu Gly Lys Gln Ala Cys Asp
                20                  25                  30

Val Leu Asn Ile Leu Asp Thr Thr Asn Val Glu Trp Thr Gln Tyr Asp
            35                  40                  45

Arg Val Leu Ile Gly Ala Ser Ile Arg Tyr Gly His Phe His Pro Ala
        50                  55                  60
```

Val Ala Glu Phe Val Lys Arg His Gln Arg Glu Leu Gln Gln Arg Ser
65                  70                  75                  80

Ser Gly Phe Phe Ser Val Asn Leu Thr Ala Arg Lys Pro Glu Lys Arg
                85                  90                  95

Ser Pro Glu Thr Asn Ala Tyr Thr Ala Lys Phe Leu Asn Gln Ser Pro
            100                 105                 110

Trp Gln Pro Asp Cys Cys Ala Val Phe Ala Gly Ala Leu Arg Tyr Pro
        115                 120                 125

Arg Tyr Arg Trp Phe Asp Arg Ile Met Ile Gln Leu Ile Met Arg Met
    130                 135                 140

Thr Gly Gly Glu Thr Asp Ser Ser Lys Glu Val Glu Tyr Thr Asp Trp
145                 150                 155                 160

Gln Gln Val Thr Arg Phe Ala Gln Glu Phe Ala Arg Leu Pro Gly Lys
                165                 170                 175

Thr Ser

<210> SEQ ID NO 9
<211> LENGTH: 180
<212> TYPE: PRT
<213> ORGANISM: Enterobacter cloacae

<400> SEQUENCE: 9

Met Lys Thr Leu Ile Leu Phe Ser Thr Arg Asp Gly Gln Thr Arg Glu
1               5                   10                  15

Ile Ala Ala Phe Leu Ala Ser Glu Leu Lys Glu Gln Gly Ile Tyr Ala
                20                  25                  30

Asp Val Ile Asn Leu Asn Arg Thr Glu Glu Ile Ala Trp Gln Glu Tyr
            35                  40                  45

Asp Arg Val Val Ile Gly Ala Ser Ile Arg Tyr Gly His Phe His Pro
        50                  55                  60

Ala Val Asp Arg Phe Val Lys Lys His Thr Glu Thr Leu Asn Ser Leu
65                  70                  75                  80

Pro Gly Ala Phe Phe Ser Val Asn Leu Val Ala Arg Lys Ala Glu Lys
                85                  90                  95

Arg Thr Pro Gln Thr Asn Ser Tyr Thr Arg Lys Phe Leu Leu Asn Ser
            100                 105                 110

Pro Trp Lys Pro Ala Ala Cys Ala Val Phe Ala Gly Ala Leu Arg Tyr
        115                 120                 125

Pro Arg Tyr Arg Trp Tyr Asp Arg Phe Met Ile Arg Leu Ile Met Lys
    130                 135                 140

Met Thr Gly Gly Glu Thr Asp Thr Arg Lys Glu Val Val Tyr Thr Asp
145                 150                 155                 160

Trp Ser Gln Val Ala Ser Phe Ala Arg Glu Ile Val Gln Leu Thr Arg
                165                 170                 175

Ser Ser Arg Leu
            180

<210> SEQ ID NO 10
<211> LENGTH: 177
<212> TYPE: PRT
<213> ORGANISM: Enterobacter mori

<400> SEQUENCE: 10

Met Lys Ile Leu Ile Leu Phe Ser Thr Arg Asp Gly Gln Thr Arg Glu
1               5                   10                  15

```
Ile Ala Ala Ser Leu Ala Ser Glu Leu Lys Glu Gln Ala Phe Asp Val
            20                  25                  30

Asp Val Val Asn Leu His Arg Ala Glu Asn Ile Ala Trp Glu Glu Tyr
        35                  40                  45

Asp Gly Val Val Ile Gly Ala Ser Ile Arg Tyr Gly His Phe His Ser
    50                  55                  60

Thr Leu Asn Ser Phe Val Lys Lys His Gln Gln Ala Leu Lys Lys Leu
65                  70                  75                  80

Pro Gly Ala Phe Tyr Ser Val Asn Leu Val Ala Arg Lys Pro Glu Lys
                85                  90                  95

Arg Thr Pro Gln Thr Asn Ser Tyr Thr Arg Lys Phe Leu Leu Asp Ser
            100                 105                 110

Pro Trp Gln Pro Asp Leu Ser Ala Val Phe Ala Gly Ala Leu Arg Tyr
        115                 120                 125

Pro Arg Tyr Asn Trp Tyr Asp Arg Ile Met Ile Arg Leu Ile Met Lys
    130                 135                 140

Ile Thr Gly Gly Glu Thr Asp Thr Arg Lys Glu Val Val Tyr Thr Asp
145                 150                 155                 160

Trp Gln Gln Val Thr His Phe Ala His Glu Ile Val Gln Leu Val Arg
                165                 170                 175

Lys

<210> SEQ ID NO 11
<211> LENGTH: 178
<212> TYPE: PRT
<213> ORGANISM: Enterobacter cloacae

<400> SEQUENCE: 11

Lys Ala Leu Val Leu Tyr Ser Thr Arg Asp Gly Gln Thr His Ala Ile
1               5                   10                  15

Ala Ser Tyr Ile Ala Ser Cys Met Lys Glu Lys Ala Glu Cys Asp Val
            20                  25                  30

Ile Asp Leu Thr His Gly Glu His Val Asn Leu Thr Gln Tyr Asp Gln
        35                  40                  45

Val Leu Ile Gly Ala Ser Ile Arg Tyr Gly His Phe Asn Ala Val Leu
    50                  55                  60

Asp Lys Phe Ile Lys Arg Asn Val Asp Gln Leu Asn Asn Met Pro Ser
65                  70                  75                  80

Ala Phe Phe Cys Val Asn Leu Thr Ala Arg Lys Pro Glu Lys Arg Thr
                85                  90                  95

Pro Gln Thr Asn Pro Tyr Val Arg Lys Phe Leu Leu Ala Thr Pro Trp
            100                 105                 110

Gln Pro Ala Leu Cys Gly Val Phe Ala Gly Ala Leu Arg Tyr Pro Arg
        115                 120                 125

Tyr Arg Trp Ile Asp Lys Val Met Ile Gln Leu Ile Met Arg Met Thr
    130                 135                 140

Gly Gly Glu Thr Asp Thr Ser Lys Glu Val Glu Tyr Thr Asp Trp Glu
145                 150                 155                 160

Gln Val Lys Lys Phe Ala Glu Asp Phe Ala Lys Leu Ser Tyr Lys Lys
                165                 170                 175

Ala Leu

<210> SEQ ID NO 12
<211> LENGTH: 177
<212> TYPE: PRT
```

-continued

<213> ORGANISM: Pantoea ananatis

<400> SEQUENCE: 12

Lys Ala Leu Ile Leu Phe Ser Thr Arg Asp Gly Gln Thr Gln Lys Ile
1               5                   10                  15

Ala Ser Ala Ile Ala Asp Glu Ile Lys Gly Gln Gln Ser Cys Asp Val
            20                  25                  30

Ile Asn Ile Gln Asp Ala Lys Thr Leu Asp Trp Gln Gln Tyr Asp Arg
        35                  40                  45

Val Leu Ile Gly Ala Ser Ile Arg Tyr Gly His Phe Gln Pro Val Val
    50                  55                  60

Asn Glu Phe Val Lys His Asn Leu Leu Ala Leu Gln Arg Val Ser
65                  70                  75                  80

Gly Phe Phe Ser Val Asn Leu Thr Ala Arg Lys Pro Glu Lys Arg Ser
                85                  90                  95

Pro Glu Thr Asn Ala Tyr Thr Val Lys Phe Leu Ala Gln Ser Pro Trp
            100                 105                 110

Gln Pro Asp Cys Cys Ala Val Phe Ala Gly Ala Leu Tyr Tyr Pro Arg
        115                 120                 125

Tyr Arg Trp Phe Asp Arg Val Met Ile Gln Phe Ile Met Arg Met Thr
    130                 135                 140

Gly Gly Glu Thr Asp Ala Ser Lys Glu Val Glu Tyr Thr Asp Trp Gln
145                 150                 155                 160

Gln Val Gln Arg Phe Ala Arg Asp Phe Ala Gln Leu Pro Gly Lys Ser
                165                 170                 175

Tyr

<210> SEQ ID NO 13
<211> LENGTH: 180
<212> TYPE: PRT
<213> ORGANISM: Escherichia coli

<400> SEQUENCE: 13

Lys Thr Leu Ile Leu Phe Ser Thr Arg Asp Gly Gln Thr Arg Glu Ile
1               5                   10                  15

Ala Ser Tyr Leu Ala Ser Glu Leu Lys Glu Leu Gly Ile Gln Ala Asp
            20                  25                  30

Val Ala Asn Val His Arg Ile Glu Glu Pro Gln Trp Glu Asn Tyr Asp
        35                  40                  45

Arg Val Val Ile Gly Ala Ser Ile Arg Tyr Gly His Tyr His Ser Ala
    50                  55                  60

Phe Gln Glu Phe Val Lys Lys His Ala Thr Arg Leu Asn Ser Met Pro
65                  70                  75                  80

Ser Ala Phe Tyr Ser Val Asn Leu Val Ala Arg Lys Pro Glu Lys Arg
                85                  90                  95

Thr Pro Gln Thr Asn Ser Tyr Ala Arg Lys Phe Leu Met Asn Ser Gln
            100                 105                 110

Trp Arg Pro Asp Arg Cys Ala Val Ile Ala Gly Ala Leu Arg Tyr Pro
        115                 120                 125

Arg Tyr Arg Trp Tyr Asp Arg Phe Met Ile Lys Leu Ile Met Lys Met
    130                 135                 140

Ser Gly Gly Glu Thr Asp Thr Arg Lys Glu Val Val Tyr Thr Asp Trp
145                 150                 155                 160

Glu Gln Val Ala Asn Phe Ala Arg Glu Ile Ala His Leu Thr Asp Lys
                165                 170                 175

Pro Thr Leu Lys
          180

<210> SEQ ID NO 14
<211> LENGTH: 177
<212> TYPE: PRT
<213> ORGANISM: Erwinia toletana

<400> SEQUENCE: 14

Lys Ala Leu Ile Leu Phe Ser Ser Arg Glu Gly Gln Thr Arg Glu Ile
1               5                   10                  15

Ala Ser Tyr Ile Ala Asn Ser Ile Lys Glu Glu Met Glu Cys Asp Val
            20                  25                  30

Phe Asn Ile Leu Arg Val Glu Gln Ile Asp Trp Ser Gln Tyr Asp Arg
        35                  40                  45

Val Leu Ile Gly Gly Ser Ile His Tyr Gly His Phe His Pro Ala Val
    50                  55                  60

Ala Lys Phe Val Lys Arg His Leu His Glu Leu Gln Gln Arg Ser Ser
65                  70                  75                  80

Gly Phe Phe Cys Val Asn Leu Thr Ala Arg Lys Ala Asp Lys Arg Thr
                85                  90                  95

Pro Gln Thr Asn Ala Tyr Met Arg Lys Phe Leu Leu Gln Ser Pro Trp
            100                 105                 110

Gln Pro Asp Cys Cys Ala Val Phe Ala Gly Ala Leu Arg Tyr Thr Arg
        115                 120                 125

Tyr Arg Trp Phe Asp Arg Val Met Ile Gln Leu Ile Met Arg Met Thr
    130                 135                 140

Gly Gly Glu Thr Asp Thr Ser Lys Glu Val Glu Tyr Thr Asp Trp Thr
145                 150                 155                 160

Gln Val Ala Arg Phe Ala Gln Glu Phe Ala His Leu Pro Gly Lys Thr
                165                 170                 175

Gln

<210> SEQ ID NO 15
<211> LENGTH: 178
<212> TYPE: PRT
<213> ORGANISM: Pectobacterium carotovorum

<400> SEQUENCE: 15

Lys Ala Leu Ile Val Phe Ser Ser Arg Asp Gly Gln Thr Arg Ala Ile
1               5                   10                  15

Ala Ser Tyr Ile Ala Asn Thr Leu Lys Gly Thr Leu Glu Cys Asp Val
            20                  25                  30

Val Asn Val Leu Asn Ala Asn Asp Ile Asp Leu Ser Gln Tyr Asp Arg
        35                  40                  45

Val Ala Ile Gly Ala Ser Ile Arg Tyr Gly Arg Phe His Pro Ala Val
    50                  55                  60

Asn Gln Phe Ile Arg Lys His Leu Thr Ser Leu Gln Gln Leu Pro Ser
65                  70                  75                  80

Ala Phe Phe Ser Val Asn Leu Thr Ala Arg Lys Pro Glu Lys Arg Thr
                85                  90                  95

Ile Gln Thr Asn Ala Tyr Thr Arg Lys Phe Leu Leu Asn Ser Pro Trp
            100                 105                 110

Gln Pro Asp Leu Cys Cys Val Phe Ala Gly Ala Leu Arg Tyr Pro Arg
        115                 120                 125

```
Tyr Arg Trp Phe Asp Arg Val Met Ile Gln Leu Ile Met Arg Ile Thr
            130                 135                 140

Gly Gly Glu Thr Asp Ser Thr Lys Glu Ile Glu Tyr Thr Asp Trp Gln
145                 150                 155                 160

Gln Val Ala Arg Phe Ala Gln Asp Phe Ala Gln Leu Ala Ala Lys Asn
                165                 170                 175

Pro Ala

<210> SEQ ID NO 16
<211> LENGTH: 178
<212> TYPE: PRT
<213> ORGANISM: Shimwellia blattae

<400> SEQUENCE: 16

Lys Thr Leu Ile Leu Phe Ser Thr Arg Asp Gly Gln Thr His Lys Ile
1               5                   10                  15

Ala Arg His Ile Ala Gly Val Leu Glu Glu Gln Gly Lys Ala Cys Glu
                20                  25                  30

Leu Val Asp Leu Leu Gln Pro Gly Glu Pro Asp Trp Ser Thr Val Glu
            35                  40                  45

Cys Val Val Leu Gly Ala Ser Ile Arg Tyr Gly His Phe His Lys Ser
    50                  55                  60

Phe Ile Arg Phe Val Asn Thr His Ala Gln Arg Leu Asn Asn Met Pro
65                  70                  75                  80

Gly Ala Leu Phe Thr Val Asn Leu Val Ala Arg Lys Pro Glu Lys Gln
                85                  90                  95

Ser Pro Gln Thr Asn Ser Tyr Thr Arg Lys Phe Leu Ala Ala Ser Pro
                100                 105                 110

Trp Gln Pro Gln Arg Cys Gln Val Phe Ala Gly Ala Leu Arg Tyr Pro
            115                 120                 125

Arg Tyr Ser Trp Tyr Asp Arg Met Met Ile Arg Leu Ile Met Lys Met
            130                 135                 140

Ala Gly Gly Glu Thr Asp Thr Arg Lys Glu Val Glu Tyr Thr Asp Trp
145                 150                 155                 160

Gln Ser Val Thr Arg Phe Ala Arg Glu Ile Ala Gln Leu Pro Gly Glu
                165                 170                 175

Thr Arg

<210> SEQ ID NO 17
<211> LENGTH: 179
<212> TYPE: PRT
<213> ORGANISM: Enterobacter cloacae

<400> SEQUENCE: 17

Lys Thr Leu Ile Leu Phe Ser Thr Arg Asp Gly Gln Thr Arg Glu Ile
1               5                   10                  15

Ala Ala Phe Leu Ala Ser Glu Leu Lys Glu Gln Gly Ile Tyr Ala Asp
                20                  25                  30

Val Ile Asn Leu Asn Arg Thr Glu Glu Ile Ala Trp Gln Glu Tyr Asp
            35                  40                  45

Arg Val Val Ile Gly Ala Ser Ile Arg Tyr Gly His Phe His Pro Ala
    50                  55                  60

Val Asp Arg Phe Val Lys Lys His Thr Glu Thr Leu Asn Ser Leu Pro
65                  70                  75                  80

Gly Ala Phe Phe Ser Val Asn Leu Val Ala Arg Lys Ala Glu Lys Arg
                85                  90                  95
```

```
Thr Pro Gln Thr Asn Ser Tyr Thr Arg Lys Phe Leu Leu Asn Ser Pro
                100                 105                 110

Trp Lys Pro Ala Ala Cys Ala Val Phe Ala Gly Ala Leu Arg Tyr Pro
            115                 120                 125

Arg Tyr Arg Trp Tyr Asp Arg Phe Met Ile Arg Leu Ile Met Lys Met
130                 135                 140

Thr Gly Gly Glu Thr Asp Thr Arg Lys Glu Val Val Tyr Thr Asp Trp
145                 150                 155                 160

Ser Gln Val Ala Ser Phe Ala Arg Glu Ile Val Gln Leu Thr Arg Ser
                165                 170                 175

Ser Arg Leu

<210> SEQ ID NO 18
<211> LENGTH: 178
<212> TYPE: PRT
<213> ORGANISM: Artificial Sequence
<220> FEATURE:
<223> OTHER INFORMATION: Recombinant

<400> SEQUENCE: 18

Lys Ala Leu Val Leu Tyr Ser Thr Arg Asp Gly Gln Thr His Ala Ile
1               5                   10                  15

Ala Ser Tyr Ile Ala Ser Cys Met Lys Glu Lys Ala Glu Cys Asp Val
                20                  25                  30

Ile Asp Leu Thr His Gly Glu His Val Asn Leu Thr Gln Tyr Asp Gln
            35                  40                  45

Val Leu Ile Gly Ala Asn Ile Arg Tyr Gly His Phe Asn Ala Val Leu
    50                  55                  60

Asp Lys Phe Ile Lys Arg Asn Val Asp Gln Leu Asn Asn Met Pro Ser
65                  70                  75                  80

Ala Phe Phe Cys Val Asn Leu Thr Ala Arg Lys Pro Glu Lys Arg Thr
                85                  90                  95

Pro Gln Thr Asn Pro Tyr Val Arg Lys Phe Leu Leu Ala Thr Pro Trp
                100                 105                 110

Gln Pro Ala Leu Cys Gly Val Phe Ala Gly Ala Leu Arg Tyr Pro Arg
            115                 120                 125

Tyr Arg Trp Ile Asp Lys Val Met Ile Gln Leu Ile Met Arg Met Thr
130                 135                 140

Gly Gly Glu Thr Asp Thr Ser Lys Glu Val Glu Tyr Thr Asp Trp Glu
145                 150                 155                 160

Gln Val Lys Lys Phe Ala Glu Asp Phe Ala Lys Leu Ser Tyr Lys Lys
                165                 170                 175

Ala Leu

<210> SEQ ID NO 19
<211> LENGTH: 172
<212> TYPE: PRT
<213> ORGANISM: Artificial Sequence
<220> FEATURE:
<223> OTHER INFORMATION: Recombinant

<400> SEQUENCE: 19

Lys Ala Leu Val Leu Tyr Ser Thr Arg Asp Gly Gln Thr His Ala Ile
1               5                   10                  15

Ala Ser Tyr Ile Ala Ser Cys Met Lys Glu Lys Ala Glu Cys Asp Val
                20                  25                  30
```

Ile Asp Leu Thr His Gly Glu His Val Asn Leu Thr Gln Tyr Asp Gln
            35                  40                  45

Val Leu Ile Gly Ala Ser Ile Arg Tyr Gly His Phe Asn Ala Val Leu
 50                  55                  60

Asp Lys Phe Ile Lys Arg Asn Val Asp Gln Leu Asn Asn Met Pro Ser
 65                  70                  75                  80

Ala Phe Phe Cys Val Asn Leu Thr Ala Arg Lys Pro Glu Lys Arg Thr
                85                  90                  95

Pro Gln Thr Asn Pro Tyr Val Arg Lys Phe Leu Leu Ala Thr Pro Trp
                100                 105                 110

Gln Pro Ala Leu Cys Gly Val Phe Ala Gly Ala Leu Arg Tyr Pro Arg
                115                 120                 125

Tyr Arg Trp Ile Asp Lys Val Met Ile Gln Leu Ile Met Arg Met Thr
            130                 135                 140

Gly Gly Glu Thr Asp Thr Ser Lys Glu Val Glu Tyr Thr Asp Trp Glu
145                 150                 155                 160

Gln Val Lys Lys Phe Ala Glu Asp Phe Ala Lys Leu
                165                 170

<210> SEQ ID NO 20
<211> LENGTH: 179
<212> TYPE: PRT
<213> ORGANISM: Artificial Sequence
<220> FEATURE:
<223> OTHER INFORMATION: Recombinant

<400> SEQUENCE: 20

Lys Thr Leu Ile Leu Phe Ser Thr Arg Asp Gly Gln Thr Arg Glu Ile
 1               5                   10                  15

Ala Ala Phe Leu Ala Ser Glu Leu Lys Glu Gln Gly Ile Tyr Ala Asp
                20                  25                  30

Val Ile Asn Leu Asn Arg Thr Glu Glu Ile Ala Trp Gln Glu Tyr Asp
            35                  40                  45

Arg Val Val Ile Gly Ala Ser Ile Arg Tyr Gly His Phe His Pro Ala
 50                  55                  60

Val Asp Arg Phe Val Lys Lys His Thr Glu Thr Leu Asn Ser Leu Pro
 65                  70                  75                  80

Gly Ala Phe Phe Ser Val Asn Leu Val Ala Arg Lys Ala Glu Lys Arg
                85                  90                  95

Thr Pro Gln Thr Asn Ser Tyr Thr Arg Lys Phe Leu Leu Asn Ser Pro
                100                 105                 110

Trp Lys Pro Ala Ala Cys Ala Val Phe Ala Gly Ala Leu Arg Tyr Pro
            115                 120                 125

Arg Tyr Arg Trp Tyr Asp Arg Phe Met Ile Arg Leu Ile Met Lys Met
            130                 135                 140

Thr Gly Gly Glu Thr Asp Thr Arg Lys Glu Val Val Tyr Thr Asp Trp
145                 150                 155                 160

Ser Gln Ile Ala Ser Phe Ala Arg Glu Ile Val Gln Leu Thr Arg Ser
                165                 170                 175

Ser Arg Leu

<210> SEQ ID NO 21
<211> LENGTH: 504
<212> TYPE: PRT
<213> ORGANISM: Amaranthus tuberculatus

<400> SEQUENCE: 21

```
Met Gly Asn Ile Ser Glu Arg Glu Pro Thr Ser Ala Lys Arg Val
1               5                   10                  15

Ala Val Val Gly Ala Val Ser Gly Leu Ala Ala Tyr Lys Leu
            20                  25                  30

Lys Ser His Gly Leu Ser Val Thr Leu Phe Glu Ala Asp Ser Arg Ala
            35                  40                  45

Gly Gly Lys Leu Lys Thr Val Lys Lys Asp Gly Phe Ile Trp Asp Glu
            50                  55                  60

Gly Ala Asn Thr Met Thr Glu Ser Glu Ala Glu Val Ser Ser Leu Ile
65                      70                  75                  80

Asp Asp Leu Gly Leu Arg Glu Lys Gln Gln Leu Pro Ile Ser Gln Asn
                85                  90                  95

Lys Arg Tyr Ile Ala Arg Asp Gly Leu Pro Val Leu Leu Pro Ser Asn
                100                 105                 110

Pro Ala Ala Leu Leu Thr Ser Asn Ile Leu Ser Ala Lys Ser Lys Leu
            115                 120                 125

Gln Ile Met Leu Glu Pro Phe Leu Trp Arg Lys His Asn Ala Thr Glu
            130                 135                 140

Leu Ser Asp Glu His Val Gln Glu Ser Val Gly Glu Phe Phe Glu Arg
145                 150                 155                 160

His Phe Gly Lys Glu Phe Val Asp Tyr Val Ile Asp Pro Phe Val Ala
                165                 170                 175

Gly Thr Cys Gly Gly Asp Pro Gln Ser Leu Ser Met His His Thr Phe
            180                 185                 190

Pro Glu Val Trp Asn Ile Glu Lys Arg Phe Gly Ser Val Phe Ala Gly
            195                 200                 205

Leu Ile Gln Ser Thr Leu Leu Ser Lys Lys Glu Lys Gly Gly Glu Asn
210                 215                 220

Ala Ser Ile Lys Lys Pro Arg Val Arg Gly Ser Phe Ser Phe Gln Gly
225                 230                 235                 240

Gly Met Gln Thr Leu Val Asp Thr Met Cys Lys Gln Leu Gly Glu Asp
            245                 250                 255

Glu Leu Lys Leu Gln Cys Glu Val Leu Ser Leu Ser Tyr Asn Gln Lys
            260                 265                 270

Gly Ile Pro Ser Leu Gly Asn Trp Ser Val Ser Ser Met Ser Asn Asn
            275                 280                 285

Thr Ser Glu Asp Gln Ser Tyr Asp Ala Val Val Val Thr Ala Pro Ile
            290                 295                 300

Arg Asn Val Lys Glu Met Lys Ile Met Lys Phe Gly Asn Pro Phe Ser
305                 310                 315                 320

Leu Asp Phe Ile Pro Glu Val Thr Tyr Val Pro Leu Ser Val Met Ile
            325                 330                 335

Thr Ala Phe Lys Lys Asp Lys Val Lys Arg Pro Leu Glu Gly Phe Gly
            340                 345                 350

Val Leu Ile Pro Ser Lys Glu Gln His Asn Gly Leu Lys Thr Leu Gly
            355                 360                 365

Thr Leu Phe Ser Ser Met Met Phe Pro Asp Arg Ala Pro Ser Asp Met
            370                 375                 380

Cys Leu Phe Thr Thr Phe Val Gly Gly Ser Arg Asn Arg Lys Leu Ala
385                 390                 395                 400

Asn Ala Ser Thr Asp Glu Leu Lys Gln Ile Val Ser Ser Asp Leu Gln
                405                 410                 415
```

Gln Leu Leu Gly Thr Glu Asp Glu Pro Ser Phe Val Asn His Leu Phe
            420                 425                 430

Trp Ser Asn Ala Phe Pro Leu Tyr Gly His Asn Tyr Asp Ser Val Leu
            435                 440                 445

Arg Ala Ile Asp Lys Met Glu Lys Asp Leu Pro Gly Phe Phe Tyr Ala
            450                 455                 460

Gly Asn His Lys Gly Gly Leu Ser Val Gly Lys Ala Met Ala Ser Gly
465                 470                 475                 480

Cys Lys Ala Ala Glu Leu Val Ile Ser Tyr Leu Asp Ser His Ile Tyr
                485                 490                 495

Val Lys Met Asp Glu Lys Thr Ala
            500

<210> SEQ ID NO 22
<211> LENGTH: 537
<212> TYPE: DNA
<213> ORGANISM: Artificial Sequence
<220> FEATURE:
<223> OTHER INFORMATION: Recombinant

<400> SEQUENCE: 22
atgaaagcgc tggtgctgta tagcacccgc gatggccaga cccatgcgat tgcgagctat      60
attgcgagct gcatgaaaga aaaagcggaa tgcgatgtga ttgatctgac ccatggcgaa     120
catgtgaacc tgacccagta tgatcaggtg ctgattggcg cgagcattcg ctatggccat     180
tttaacgcgg tgctggataa atttattaaa cgcaacgtgg atcagctgaa caacatgccg     240
agcgcgtttt tttgcgtgaa cctgaccgcg cgcaaaccgg aaaaacgcac cccgcagacc     300
aacccgtatg tgcgcaaatt tctgctggcg accccgtggc agccggcgct gtgcggcgtg     360
tttgcgggcg cgctgcgcta tccgcgctat cgctggattg ataaagtgat gattcagctg     420
attatgcgca tgaccggcgg cgaaaccgat accagcaaag aagtggaata taccgattgg     480
gaacaggtga aaaatttgc ggaagatttt gcgaaactga gctataaaaa agcgctg        537

<210> SEQ ID NO 23
<211> LENGTH: 534
<212> TYPE: DNA
<213> ORGANISM: Artificial Sequence
<220> FEATURE:
<223> OTHER INFORMATION: Recombinant

<400> SEQUENCE: 23
atgaaagcgc tgattctgtt tagcacccgc gatggccaga cccagaaaat tgcgagcgcg      60
attgcggatg aaattaaagg ccagcagagc tgcgatgtga ttaacattca ggatgcgaaa     120
accctggatt ggcagcagta tgatcgcgtg ctgattggcg cgagcattcg ctatggccat     180
tttcagccgg tggtgaacga atttgtgaaa cataacctgc tggcgctgca gcagcgcgtg     240
agcggctttt ttagcgtgaa cctgaccgcg cgcaaaccgg aaaaacgcag cccgaaaacc     300
aacgcgtata ccgtgaaatt tctggcgcag agcccgtggc agccggattg ctgcgcggtg     360
tttgcgggcg cgctgtatta tccgcgctat cgctggtttg atcgcgtgat gattcagttt     420
attatgcgca tgaccggcgg cgaaaccgat gcgagcaaag aagtggaata taccgattgg     480
cagcaggtgc agcgctttgc gcgcgatttt gcgcagctgc cgggcaaaag ctat          534

<210> SEQ ID NO 24
<211> LENGTH: 531
<212> TYPE: DNA
<213> ORGANISM: Artificial Sequence

```
<220> FEATURE:
<223> OTHER INFORMATION: Recombinant

<400> SEQUENCE: 24
atgaaagcgc tgattctgta tagcacccgc gatggccaga cccgcaaaat tgcgagcagc      60
attgcggatg tgattcgcca gcagcagcag tgcgatgtgc tgaacattaa agatgcgagc     120
ctgccggatt gggcgcagta tgatcgcgtg ctgattggcg cgagcattcg ctatggccat     180
tttcagccgg tggtggataa atttgtgaaa cagcatctgc atgaactgca gcagcgcacc     240
agcggctttt ttagcgtgaa cctgaccgcg cgcaaaccgg aaaaacgcag cccggaaacc     300
aacgcgtata cccagaaatt tctggcgcat agcccgtggc agccggattg ctgcgcggtg     360
tttgcgggcg cgctgtatta tccgcgctat cgctggtttg atcgcgtgat gattcagctg     420
attatgcgca tgaccggcgg cgaaaccgat agcaccaaag aagtggaata taccgattgg     480
cagcaggtga gcacctttgc gaacgatttt gcgcagctgc cgggcaaaag c              531

<210> SEQ ID NO 25
<211> LENGTH: 546
<212> TYPE: DNA
<213> ORGANISM: Escherichia coli

<400> SEQUENCE: 25
gtgaaaacat taattctttt ctcaacaagg gacggacaaa cgcgcgagat tgcctcctac      60
ctggcttcgg aactgaaaga actggggatc caggcggatg tcgccaatgt gcaccgcatt     120
gaagaaccac agtgggaaaa ctatgaccgt gtggtcattg gtgcttctat cgctatggt      180 cactaccatt cagcgttcca ggaatttgtc aaaaaacatg cgacgcggct gaattcgatg     240
ccgagcgcct tttactccgt gaatctggtg gcgcgcaaac cggagaagcg tactccacag     300
accaacagct acgcgcgcaa gtttctgatg aactcgcaat ggcgtcccga tcgctgcgcg     360
gtcattgccg gggcgctgcg ttacccacgt tatcgctggt acgaccgttt tatgatcaag     420
ctgattatga agatgtcagg cggtgaaacg gatacgcgca agaagttgt ctataccgat     480 tgggagcagg tggcgaattt cgcccgagaa atcgcccatt aaccgacaa accgacgctg     540 aaataa                                                               546

<210> SEQ ID NO 26
<211> LENGTH: 534
<212> TYPE: DNA
<213> ORGANISM: Artificial Sequence
<220> FEATURE:
<223> OTHER INFORMATION: Recombinant

<400> SEQUENCE: 26
atgaaagcgc tgattctgtt tagcagccgc gaaggccaga cccgcgaaat tgcgagctat      60
attgcgaaca gcattaaaga agaaatggaa tgcgatgtgt taacattct gcgcgtggaa     120 cagattgatt ggagccagta tgatcgcgtg ctgattggcg cagcattca ttatggccat     180 tttcatccgg cggtggcgaa atttgtgaaa cgccatctgc atgaactgca gcagcgcagc     240
agcggctttt tttgcgtgaa cctgaccgcg cgcaaagcgg ataaacgcac cccgcagacc     300
aacgcgtata tgcgcaaatt tctgctgcag agcccgtggc agccggattg ctgcgcggtg     360
tttgcgggcg cgctgcgcta taccgcgtat cgctggtttg atcgcgtgat gattcagctg     420
attatgcgca tgaccggcgg cgaaaccgat accagcaaag aagtggaata taccgattgg     480
acccaggtgg cgcgctttgc gcaggaattt gcgcatctgc cgggcaaaac ccag           534
```

<210> SEQ ID NO 27
<211> LENGTH: 537
<212> TYPE: DNA
<213> ORGANISM: Artificial Sequence
<220> FEATURE:
<223> OTHER INFORMATION: Recombinant

<400> SEQUENCE: 27

| | | | | | |
|---|---|---|---|---|---|
| atgaaagcgc | tgattgtgtt | tagcagccgc | gatggccaga | cccgcgcgat | tgcgagctat | 60 |
| attgcgaaca | ccctgaaagg | caccctggaa | tgcgatgtgg | tgaacgtgct | gaacgcgaac | 120 |
| gatattgatc | tgagccagta | tgatcgcgtg | gcgattggcg | cgagcattcg | ctatggccgc | 180 |
| tttcatccgg | cggtgaacca | gtttattcgc | aaacatctga | ccagcctgca | gcagctgccg | 240 |
| agcgcgtttt | ttagcgtgaa | cctgaccgcg | cgcaaaccgg | aaaaacgcac | cattcagacc | 300 |
| aacgcgtata | cccgcaaatt | tctgctgaac | agcccgtggc | agccggatct | gtgctgcgtg | 360 |
| tttgcgggcg | cgctgcgcta | tccgcgctat | cgctggtttg | atcgcgtgat | gattcagctg | 420 |
| attatgcgca | ttaccggcgg | cgaaaccgat | agcaccaaag | aaattgaata | taccgattgg | 480 |
| cagcaggtgg | cgcgctttgc | gcaggatttt | gcgcagctgg | cggcgaaaaa | cccggcg | 537 |

<210> SEQ ID NO 28
<211> LENGTH: 537
<212> TYPE: DNA
<213> ORGANISM: Artificial Sequence
<220> FEATURE:
<223> OTHER INFORMATION: Recombinant

<400> SEQUENCE: 28

| | | | | | |
|---|---|---|---|---|---|
| atgaagacct | tgatcctatt | ctccaccagg | gacggccaaa | cacacaagat | cgcaaggcac | 60 |
| atcgcaggag | tcctcgaaga | gcaggggaag | gcctgcgagt | tggtcgatct | gttacagccc | 120 |
| ggcgaaccag | actggagtac | cgttgaatgc | gtcgttctag | ggccagcat | tagatatggt | 180 |
| cacttccata | agtctttcat | caggttcgta | aacactcacg | cgcagcgctt | gaataatatg | 240 |
| ccaggcgccc | ttttcacagt | taacttagtc | gcccgaaagc | ccgagaagca | gagtccacag | 300 |
| acgaactctt | acacccgcaa | gtttctcgcc | gcctcccctt | ggcagccaca | gcgatgccaa | 360 |
| gttttcgcgg | gcgctttgag | gtaccctagg | tactcgtggt | acgacagaat | gatgatacgt | 420 |
| tgataatga | agatggccgg | gggcgagact | gacacaagga | aggaggttga | gtacactgac | 480 |
| tggcagtcgg | tgactcggtt | cgcgagggag | atcgctcagc | tgccgggaga | gacgcgg | 537 |

<210> SEQ ID NO 29
<211> LENGTH: 534
<212> TYPE: DNA
<213> ORGANISM: Artificial Sequence
<220> FEATURE:
<223> OTHER INFORMATION: Recombinant

<400> SEQUENCE: 29

| | | | | | |
|---|---|---|---|---|---|
| atgaaagcgc | tgattctgtt | tagcagccgc | gatggccaga | cccagctgat | tgcgagcagc | 60 |
| attgcgaaag | aactggaagg | caaacaggcg | tgcgatgtgc | tgaacattct | ggataccacc | 120 |
| aacgtggaat | ggaccccagta | tgatcgcgtg | ctgattggcg | cgagcattcg | ctatggccat | 180 |
| tttcatccgg | cggtggcgga | atttgtgaaa | cgccatcagc | gcgaactgca | gcagcgcagc | 240 |
| agcggctttt | ttagcgtgaa | cctgaccgcg | cgcaaaccgg | aaaaacgcag | cccggaaacc | 300 |
| aacgcgtata | ccgcgaaatt | tctgaaccag | agcccgtggc | agccggattg | ctgcgcggtg | 360 |
| tttgcgggcg | cgctgcgcta | tccgcgctat | cgctggtttg | atcgcattat | gattcagctg | 420 |

```
attatgcgca tgaccggcgg cgaaaccgat agcagcaaag aagtggaata taccgattgg    480
cagcaggtga cccgctttgc gcaggaattt gcgcgcctgc cgggcaaaac cagc          534
```

<210> SEQ ID NO 30
<211> LENGTH: 540
<212> TYPE: DNA
<213> ORGANISM: Artificial Sequence
<220> FEATURE:
<223> OTHER INFORMATION: Recombinant

<400> SEQUENCE: 30

```
atgaaaaccc tgattctgtt tagcacccgc gatggccaga cccgcgaaat tgcggcgttt     60
ctggcgagcg aactgaaaga cagggcatt tatgcggatg tgattaacct gaaccgcacc    120
gaagaaattg cgtggcagga atatgatcgc gtggtgattg cgcgagcat tcgctatggc    180 cattttcatc cggcggtgga tcgctttgtg aaaaaacata ccgaaaccct gaacagcctg    240
ccgggcgcgt tttttagcgt gaacctggtg gcgcgcaaag cggaaaaacg cacccccgcag   300 accaacagct ataccgcaa atttctgctg aacagcccgt ggaaaccggc ggcgtgcgcg    360
gtgtttgcgg gcgcgctgcg ctatccgcgc tatcgctggt atgatcgctt tatgattcgc    420
ctgattatga aaatgaccgg cggcgaaacc gatacccgca agaagtggt gtataccgat    480 tggagccagg tggcgagctt tgcgcgcgaa attgtgcagc tgacccgcag cagccgcctg    540
```

<210> SEQ ID NO 31
<211> LENGTH: 531
<212> TYPE: DNA
<213> ORGANISM: Artificial Sequence
<220> FEATURE:
<223> OTHER INFORMATION: Recombinant

<400> SEQUENCE: 31

```
atgaaaattc tgattctgtt tagcacccgc gatggccaga cccgcgaaat tgcggcgagc     60
ctggcgagcg aactgaaaga caggcgtttt gatgtggatg tggtgaacct gcatcgcgcg    120
gaaaacattg cgtgggaaga atatgatggc gtggtgattg cgcgcgagcat tcgctatggc   180 cattttcata gcaccctgaa cagctttgtg aaaaaacatc agcaggcgct gaaaaaactg    240
ccgggcgcgt tttatagcgt gaacctggtg gcgcgcaaac cggaaaaacg cacccccgcag   300 accaacagct ataccgcaa atttctgctg gatagcccgt ggcagccgga tctgagcgcg    360
gtgtttgcgg gcgcgctgcg ctatccgcgc tataactggt atgatcgcat tatgattcgc    420
ctgattatga aaattaccgg cggcgaaacc gatacccgca agaagtggt gtataccgat    480 tggcagcagg tgacccattt tgcgcatgaa attgtgcagc tggtgcgcaa a              531
```

<210> SEQ ID NO 32
<211> LENGTH: 540
<212> TYPE: DNA
<213> ORGANISM: Artificial Sequence
<220> FEATURE:
<223> OTHER INFORMATION: Recombinant

<400> SEQUENCE: 32

```
atgaaggcct tggtactgta ctcgacgcgg gacggccaga cccacgcaat tgcttcatac     60
atcgcctcct gcatgaagga gaaggccgaa tgcgacgtga tcgacctcac ccacggggag    120
cacgtgaacc tcacccaata cgatcaggtg ctaatcggtg cgagtattcg ttacggccac    180
ttcaacgccg tgcttgacaa gttcatcaag agaaacgtgg atcagctgaa caacatgcca    240
```

```
agcgcgttct tctgcgtaaa cctcacagca aggaagcccg agaagcgtac tccccagaca    300
aacccttatg tccgaaaatt cttgcttgct acccctggc agcccgcgtt gtgcggagtg     360
ttcgcagggg cccttcggta cccgcgatac cggtggatcg acaaggtgat gatccagcta    420
ataatgcgga tgactggggg agagacagac acgagcaagg aggtcgagta cacggattgg    480
gagcaggtta agaagttcgc ggaggatttt gcaaagctat cgtacaagaa ggccctctag    540
```

<210> SEQ ID NO 33
<211> LENGTH: 537
<212> TYPE: DNA
<213> ORGANISM: Artificial Sequence
<220> FEATURE:
<223> OTHER INFORMATION: Recombinant

<400> SEQUENCE: 33

```
atgaaggcct tgatcctgtt ctctacacgc gacggacaga cacagaagat cgcatctgcc     60
atcgctgatg agataaaggg gcagcaatcg tgcgacgtga ttaacataca ggatgccaaa    120
accctcgact ggcagcagta cgaccgggta ctcatcggcg cctccattcg ttacgggcat    180
ttccagcccg ttgtgaatga gtttgtcaag cacaacctct ggccctaca gcagagagtt     240 tccggattct tctccgtgaa cttgacagcc cgaaagccag agaagcggag ccccgagact    300
aacgcttata cagtcaaatt cttggcgcag tcaccctggc aaccggactg ctgcgctgtt    360
tttgcggggg ccctgtacta cccacggtac cggtggttcg atagggtgat gatacagttc    420
ataatgcgaa tgacgggggg agagaccgac gcatcgaaag aggtggagta cactgactgg    480
cagcaggtgc agcggttcgc gcgagacttc gcgcagttac cgggtaagtc ctactga       537
```

<210> SEQ ID NO 34
<211> LENGTH: 534
<212> TYPE: DNA
<213> ORGANISM: Artificial Sequence
<220> FEATURE:
<223> OTHER INFORMATION: Recombinant

<400> SEQUENCE: 34

```
atgaaggcgc tgatcttgta ctcaaccagg gacggtcaga ctcgcaagat tgcaagtagc     60
attgcggacg tcatcaggca gcagcagcag tgcgacgtct aaacattaa agacgcatca    120 cttcctgact gggcccaata tgaccgagtg ctcatcggag ctagcatccg ttacgggcat    180
ttccagcccg ttgtagacaa gttcgtgaag cagcacttgc acgagcttca gcagcggacc    240
tccggcttct tctccgtgaa cctgacggcg aggaagcctg aaaaaaggag ccctgagacc    300
aatgcctaca cccagaaatt cttggcgcac tccccttggc agcccgattg ctgtgccgtt    360
ttcgcggggg cccttttacta ccccaggtac cgttggttcg accgggtgat gatccagttg    420
attatgcgca tgactggtgg agagaccgac tctaccaagg aagtggagta cactgactgg    480
cagcaggtga gtaccttcgc caacgatttt gcccagcttc aggcaagag ctaa           534
```

<210> SEQ ID NO 35
<211> LENGTH: 546
<212> TYPE: DNA
<213> ORGANISM: Artificial Sequence
<220> FEATURE:
<223> OTHER INFORMATION: Recombinant

<400> SEQUENCE: 35

```
atgaagacct tgattctatt ctccacaagg gacggccaga ctagggagat cgcttcctac     60
ctggccagcg agctaaagga gcttggcatt caggcagacg tggctaacgt gcaccgaatt    120
```

```
gaggagccgc agtgggagaa ctacgatcgg gtcgtgatcg gcgccagcat ccggtatgga    180
cactaccaca gcgcgttcca ggagttcgtg aaaaagcacg cgacccgtct gaatagcatg    240
ccatcagcgt tctactcggt caacctcgtg gctcgtaagc ccgagaagcg gacaccccag    300
accaactcgt atgccaggaa gttccttatg aactcgcagt ggcgaccgga ccgctgcgcg    360
gtgatcgccg gtgcgctcag gtaccctcgt tataggtggt acgacaggtt tatgattaaa    420
cttataatga aaatgagcgg cggagagacc gacaccagaa aagaggtggt ttacacagac    480
tgggagcagg tagcaaactt cgctagggag attgctcacc tcaccgacaa gccgaccttg    540
aagtaa                                                               546
```

```
<210> SEQ ID NO 36
<211> LENGTH: 537
<212> TYPE: DNA
<213> ORGANISM: Artificial Sequence
<220> FEATURE:
<223> OTHER INFORMATION: Recombinant

<400> SEQUENCE: 36
```

```
atgaaggccc ttatactgtt cagttccaga gaaggccaga cgagggagat agcgagttac     60
attgccaact cgataaagga ggaaatggaa tgcgacgtgt tcaacatcct tcgtgtggag    120
cagatcgact ggtctcaata cgaccgcgtc ctgatcgggg gctcgataca ctacggccat    180
ttccacccag cggtggcaaa atttgtcaag aggcacctcc atgagttgca acagaggtct    240
tccggctttt tctgcgtcaa cctgacggcc aggaaggccg acaagcggac tccccagacc    300
aatgcctaca tgagaaagtt cttgttgcag tccccatggc aacccgattg ctgcgccgtg    360
tttgcggggg cccttaggta caccgttac aggtggttcg acaggtaat gattcagctg     420
```
(Note: small typos may exist in image — rendered as seen)
```
atcatgagga tgacgggcgg agagactgac acatcgaagg aggtggagta cacagactgg    480
acgcaggtcg cccgcttcgc gcaggagttc gcccatttgc ccggcaaaac tcagtga       537
```

```
<210> SEQ ID NO 37
<211> LENGTH: 540
<212> TYPE: DNA
<213> ORGANISM: Artificial Sequence
<220> FEATURE:
<223> OTHER INFORMATION: Recombinant

<400> SEQUENCE: 37
```

```
atgaaggctc ttatcgtatt ctcttcgagg gatggccaaa cccgagcgat cgcgtcttat     60
attgctaata ccctcaaagg gaccctagag tgcgacgtcg tcaacgtcct caatgctaac    120
gacattgatt tgagccagta cgaccgtgtg gccattggcg cctccattcg ctacgggagg    180
ttccacccag ctgttaacca gtttatccgg aagcaccttta cgagcctcca gcagctacca    240
tctgcgttct ctccgtgaa cctcacagct cggaagcccg agaagaggac tatacaaacc     300
aacgcgtaca ctaggaagtt tctactgaac tcgccgtggc agccggacct gtgctgcgtg    360
ttcgcgggag cccttcgcta tccccgttac aggtggtttg accgagtgat gattcaactc    420
ataatgcgca taacgggggg cgagacagac tccaccaagg agatcgagta caccgactgg    480
cagcaggtcg cgcgattcgc ccaggatttt gcacagcttg ccgcaaagaa cccggcatga    540
```

```
<210> SEQ ID NO 38
<211> LENGTH: 540
<212> TYPE: DNA
<213> ORGANISM: Artificial Sequence
<220> FEATURE:
```

<223> OTHER INFORMATION: Recombinant

<400> SEQUENCE: 38

```
atgaagacct tgatcctatt ctccaccagg gacggccaaa cacacaagat cgcaaggcac       60
atcgcaggag tcctcgaaga gcaggggaag gcctgcgagt tggtcgatct gttacagccc      120
ggcgaaccag actggagtac cgttgaatgc gtcgttctag gggccagcat tagatatggt      180
cacttccata agtctttcat caggttcgta aacactcacg cgcagcgctt gaataatatg      240
ccaggcgccc ttttcacagt taacttagtc gcccgaaagc ccgagaagca gagtccacag      300
acgaactctt acacccgcaa gtttctcgcc gcctcccctt ggcagccaca gcgatgccaa      360
gttttcgcgg gcgctttgag gtaccctagg tactcgtggt acgacagaat gatgatacgt      420
ttgataatga agatggccgg gggcgagact gacacaagga aggaggttga gtacactgac      480
tggcagtcgg tgactcggtt cgcgagggag atcgctcagc tgccgggaga gacgcggtag      540
```

<210> SEQ ID NO 39
<211> LENGTH: 537
<212> TYPE: DNA
<213> ORGANISM: Artificial Sequence
<220> FEATURE:
<223> OTHER INFORMATION: Recombinant

<400> SEQUENCE: 39

```
atgaaggccc taattttatt cagtagtagg gacggccaga cccagcttat agcatcgtct       60
atcgccaagg agctcgaagg gaagcaggcg tgcgacgtgt tgaatatcct cgacacgact      120
aatgtggagt ggacccagta cgaccgcgtg ctgattggag catccatccg gtacgggcac      180
tttcaccctg cggtcgccga gttcgtaaag cgtcaccagc gagagctaca gcagagaagt      240
agtggctttt tctctgtgaa cttgacggcc cgtaagccgg aaaagaggtc ccccgagact      300
aacgcctata ccgccaagtt ccttaaccaa gtccatggc agcctgactg ttgcgctgtg       360
ttcgctgggg ctttgcgata ccctcggtac cgctggttcg acagaattat gatccagcta      420
atcatgcgga tgactggggg tgagacagat tcttcaaagg aggtcgagta caccgactgg      480
cagcaggtga cccgcttcgc gcaagagttc gccaggcttc cgggaaagac cagttga        537
```

<210> SEQ ID NO 40
<211> LENGTH: 543
<212> TYPE: DNA
<213> ORGANISM: Artificial Sequence
<220> FEATURE:
<223> OTHER INFORMATION: Recombinant

<400> SEQUENCE: 40

```
atgaagaccc taatactgtt ctctacccgc gacgggcaga caagggagat cgccgcgttc       60
cttgcctcgg agctgaagga gcaggggatt tacgctgacg tcataaacct taaccggacg      120
gaggagatag cttggcagga gtatgataga gtcgtaatcg gggcgtcgat ccgatacggg      180
catttccacc ctgctgtcga ccgcttcgtg aagaagcaca cagagacact caactcactg      240
cccggcgcct ttttctctgt aaaccttgtt gcccggaaag ccgagaagag aacgccgcag      300
acgaactcat acaccaggaa gttcctatta aacagcccgt ggaagccagc ggcctgcgcg      360
gtctttgctg gggccctccg ctaccctaga taccgctggt acgacaggtt catgatacga      420
ctgattatga aaatgacagg cggggagacg gataccccgaa aggaggtagt ctacactgac      480
tggtcgcagg tcgcgtcgtt tgccagagag atagtccagt tgaccaggtc atcgcgcttg      540
tga                                                                    543
```

<210> SEQ ID NO 41
<211> LENGTH: 534
<212> TYPE: DNA
<213> ORGANISM: Artificial Sequence
<220> FEATURE:
<223> OTHER INFORMATION: Recombinant

<400> SEQUENCE: 41

```
atgaagatat taatccttttt ctccacccgt gacggccaaa cccgtgagat tgcggcgtcc      60
ttggcgtccg aactcaagga gcaggcattc gacgtggacg tcgtcaacct tcaccgggcc     120
gagaacatcg catgggagga gtacgacggt gttgtcatcg gagcgtccat caggtacggc     180
cactttcata gtaccctgaa ctcatttgtc aagaagcatc agcaggctct taagaagctt     240
cccggggctt tctacagcgt gaacctcgtc gcccggaagc tgagaagcg cacaccgcag      300 accaatagct acacccgcaa gttcctcttg gattccccgt ggcagcccga cctttcagcc     360
gtgttcgccg gggcactcag gtaccctcgg tacaattggt acgaccgtat catgattaga     420
cttatcatga agattacagg cggcgagact gataccagga aggaagtagt ctacacagac     480
tggcagcagg tcactcactt tgctcacgag atcgtccagc tcgtgcggaa gtag           534
```

<210> SEQ ID NO 42
<211> LENGTH: 537
<212> TYPE: DNA
<213> ORGANISM: Artificial Sequence
<220> FEATURE:
<223> OTHER INFORMATION: Recombinant

<400> SEQUENCE: 42

```
aaggccttgg tactgtactc gacgcgggac ggccagaccc acgcaattgc ttcatacatc      60
gcctcctgca tgaaggagaa ggccgaatgc gacgtgatcg acctcaccca cggggagcac     120
gtgaacctca cccaatacga tcaggtgcta atcggtgcga gtattcgtta cggccacttc     180
aacgccgtgc ttgacaagtt catcaagaga aacgtggatc agctgaacaa catgccaagc     240
gcgttcttct gcgtaaacct cacagcaagg aagcccgaga agcgtactcc ccagacaaac     300
ccttatgtcc gaaaattctt gcttgctacc ccctggcagc ccgcgttgtg cggagtgttc     360
gcaggggccc ttcggtaccc gcgataccgg tggatcgaca aggtgatgat ccagctaata     420
atgcggatga ctgggggaga gacagacacg agcaaggagg tcgagtacac ggattgggag     480
caggttaaga agttcgcgga ggattttgca aagctatcgt acaagaaggc cctctag        537
```

<210> SEQ ID NO 43
<211> LENGTH: 534
<212> TYPE: DNA
<213> ORGANISM: Artificial Sequence
<220> FEATURE:
<223> OTHER INFORMATION: Recombinant

<400> SEQUENCE: 43

```
aaggccttga tcctgttctc tacacgcgac ggacagacac agaagatcgc atctgccatc      60
gctgatgaga taaaggggca gcaatcgtgc gacgtgatta acatacagga tgccaaaacc     120
ctcgactggc agcagtacga ccgggtactc atcggcgcct ccattcgtta cgggcatttc     180
cagcccgttg tgaatgagtt tgtcaagcac aacctcttgg ccctacagca gagagtttcc     240
ggattcttct ccgtgaactt gacagcccga aagccagaga agcggagccc cgagactaac     300
gcttatacag tcaaattctt ggcgcagtca ccctggcaac cggactgctg cgctgttttt     360
```

| | |
|---|---|
| gcgggggccc tgtactaccc acggtaccgg tggttcgata gggtgatgat acagttcata | 420 |
| atgcgaatga cggggggaga gaccgacgca tcgaaagagg tggagtacac tgactggcag | 480 |
| caggtgcagc ggttcgcgcg agacttcgcg cagttaccgg gtaagtccta ctga | 534 |

<210> SEQ ID NO 44
<211> LENGTH: 543
<212> TYPE: DNA
<213> ORGANISM: Artificial Sequence
<220> FEATURE:
<223> OTHER INFORMATION: Recombinant

<400> SEQUENCE: 44

| | |
|---|---|
| aagaccttga ttctattctc cacaagggac ggccagacta gggagatcgc ttcctacctg | 60 |
| gccagcgagc taaaggagct tggcattcag gcagacgtgg ctaacgtgca ccgaattgag | 120 |
| gagccgcagt gggagaacta cgatcgggtc gtgatcggcg ccagcatccg gtatggacac | 180 |
| taccacagcg cgttccagga gttcgtgaaa aagcacgcga cccgtctgaa tagcatgcca | 240 |
| tcagcgttct actcggtcaa cctcgtggct cgtaagcccg agaagcggac accccagacc | 300 |
| aactcgtatg ccaggaagtt ccttatgaac tcgcagtggc gaccggaccg ctgcgcggtg | 360 |
| atcgccggtc gctcaggta ccctcgttat aggtggtacg acaggtttat gattaaactt | 420 |
| ataatgaaaa tgagcggcgg agagaccgac accagaaaag aggtggttta cacagactgg | 480 |
| gagcaggtag caaacttcgc tagggagatt gctcacctca ccgacaagcc gaccttgaag | 540 |
| taa | 543 |

<210> SEQ ID NO 45
<211> LENGTH: 534
<212> TYPE: DNA
<213> ORGANISM: Artificial Sequence
<220> FEATURE:
<223> OTHER INFORMATION: Recombinant

<400> SEQUENCE: 45

| | |
|---|---|
| aaggcccta tactgttcag ttccagagaa ggccagacga gggagatagc gagttacatt | 60 |
| gccaactcga taaggagga aatggaatgc gacgtgttca acatccttcg tgtggagcag | 120 |
| atcgactggt ctcaatacga ccgcgtcctg atcgggggct cgatacacta cggccatttc | 180 |
| cacccagcgg tggcaaaatt tgtcaagagg cacctccatg agttgcaaca gaggtcttcc | 240 |
| ggcttttct gcgtcaacct gacggccagg aaggccgaca agcggactcc ccagaccaat | 300 |
| gcctacatga gaaagttctt gttgcagtcc ccatggcaac ccgattgctg cgccgtgttt | 360 |
| gcgggggccc ttaggtacac ccgttacagg tggttcgaca gggtaatgat tcagctgatc | 420 |
| atgaggatga cggcggaga gactgacaca tcgaaggagg tggagtacac agactggacg | 480 |
| caggtcgccc gcttcgcgca ggagttcgcc catttgcccg gcaaaactca gtga | 534 |

<210> SEQ ID NO 46
<211> LENGTH: 537
<212> TYPE: DNA
<213> ORGANISM: Artificial Sequence
<220> FEATURE:
<223> OTHER INFORMATION: Recombinant

<400> SEQUENCE: 46

| | |
|---|---|
| aaggctctta tcgtattctc ttcgagggat ggccaaaccc gagcgatcgc gtcttatatt | 60 |
| gctaatacccc tcaaagggac cctagagtgc gacgtcgtca acgtcctcaa tgctaacgac | 120 |
| attgatttga gccagtacga ccgtgtggcc attggcgcct ccattcgcta cgggaggttc | 180 |

```
cacccagctg ttaaccagtt tatccggaag caccttacga gcctccagca gctaccatct    240
gcgttcttct ccgtgaacct cacagctcgg aagcccgaga agaggactat acaaaccaac    300
gcgtacacta ggaagtttct actgaactcg ccgtggcagc cggacctgtg ctgcgtgttc    360
gcgggagccc ttcgctatcc ccgttacagg tggtttgacc gagtgatgat tcaactcata    420
atgcgcataa cgggggggcga gacagactcc accaaggaga tcgagtacac cgactggcag    480
caggtcgcgc gattcgccca ggattttgca cagcttgccg caaagaaccc ggcatga       537
```

<210> SEQ ID NO 47
<211> LENGTH: 537
<212> TYPE: DNA
<213> ORGANISM: Artificial Sequence
<220> FEATURE:
<223> OTHER INFORMATION: Recombinant

<400> SEQUENCE: 47

```
aagaccttga tcctattctc caccagggac ggccaaacac acaagatcgc aaggcacatc    60
gcaggagtcc tcgaagagca ggggaaggcc tgcgagttgg tcgatctgtt acagcccggc   120
gaaccagact ggagtaccgt tgaatgcgtc gttctagggg ccagcattag atatggtcac   180
ttccataagt ctttcatcag gttcgtaaac actcacgcgc agcgcttgaa taatatgcca   240
ggcgcccttt tcacagttaa cttagtcgcc cgaaagcccg agaagcagag tccacagacg   300
aactcttaca cccgcaagtt tctcgccgcc tccccttggc agccacagcg atgccaagtt   360
ttcgcgggcg ctttgaggta ccctaggtac tcgtggtacg acagaatgat gatacgtttg   420
ataatgaaga tggccggggg cgagactgac acaaggaagg aggttgagta cactgactgg   480
cagtcggtga ctcggttcgc gagggagatc gctcagctgc cgggagagac gcggtag      537
```

<210> SEQ ID NO 48
<211> LENGTH: 540
<212> TYPE: DNA
<213> ORGANISM: Artificial Sequence
<220> FEATURE:
<223> OTHER INFORMATION: Recombinant

<400> SEQUENCE: 48

```
aagaccctaa tactgttctc tacccgcgac gggcagacaa gggagatcgc cgcgttcctt    60
gcctcggagc tgaaggagca ggggatttac gctgacgtca taaaccttaa ccggacggag   120
gagatagctt ggcaggagta tgatagagtc gtaatcgggg cgtcgatccg atacgggcat   180
ttccaccctg ctgtcgaccg cttcgtgaag aagcacacag agacactcaa ctcactgccc   240
ggcgcctttt tctctgtaaa ccttgttgcc cggaaagccg agaagagaac gccgcagacg   300
aactcataca ccaggaagtt cctattaaac agcccgtgga agccagcggc ctgcgcggtc   360
tttgctgggg ccctccgcta ccctagatac cgctggtacg acaggttcat gatacgactg   420
attatgaaaa tgacaggcgg ggagacggat acccgaaagg aggtagtcta cactgactgg   480
tcgcaggtcg cgtcgtttgc cagagagata gtccagttga ccaggtcatc gcgcttgtga   540
```

<210> SEQ ID NO 49
<211> LENGTH: 537
<212> TYPE: DNA
<213> ORGANISM: Artificial Sequence
<220> FEATURE:
<223> OTHER INFORMATION: Recombinant

<400> SEQUENCE: 49

```
aaggccttgg tactgtactc gacgcgggac ggccagaccc acgcaattgc ttcatacatc    60
gcctcctgca tgaaggagaa ggccgaatgc gacgtgatcg acctcaccca cggggagcac   120
gtgaacctca cccaatacga tcaggtgcta atcggtgcga gtattcgtta cggccacttc   180
aacgccgtgc ttgacaagtt catcaagaga aacgtggatc agctgaacaa catgccaagc   240
gcgttcttct gcgtaaacct cacggcaagg aagcccgaga agcgtactcc ccagacaaac   300
ccttatgtcc gaaaattctt gcttgctacc ccctggcagc ccgcgttgtg cggagtgttc   360
gcagggcccc ttcggtaccc gcgataccgg tggatcgaca aggtgatgat ccagctaata   420
atgcggatga ctgggggaga gacagacacg agcaaggagg tcgagtacac ggattgggag   480
caggttaaga agttcgcgga ggattttgca aagctatcgt acaagaaggc cctctag     537
```

<210> SEQ ID NO 50
<211> LENGTH: 537
<212> TYPE: DNA
<213> ORGANISM: Artificial Sequence
<220> FEATURE:
<223> OTHER INFORMATION: Recombinant

<400> SEQUENCE: 50

```
aaggccttgg tactgtactc gacgcgggac ggccagaccc acgcaattgc ttcatacatc    60
gcctcctgca tgaaggagaa ggccgaatgc gacgtgatcg acctcaccca cggggagcac   120
gtgaacctca cccaatacga tcaggtgcta atcggtgcga atattcgtta cggccacttc   180
aacgccgtgc ttgacaagtt catcaagaga aacgtggatc agctgaacaa catgccaagc   240
gcgttcttct gcgtaaacct cacagcaagg aagcccgaga agcgtactcc ccagacaaac   300
ccttatgtcc gaaaattctt gcttgctacc ccctggcagc ccgcgttgtg cggagtgttc   360
gcagggcccc ttcggtaccc gcgataccgg tggatcgaca aggtgatgat ccagctaata   420
atgcggatga ctgggggaga gacagacacg agcaaggagg tcgagtacac ggattgggag   480
caggttaaga agttcgcgga ggattttgca aagctatcgt acaagaaggc cctctag     537
```

<210> SEQ ID NO 51
<211> LENGTH: 537
<212> TYPE: DNA
<213> ORGANISM: Artificial Sequence
<220> FEATURE:
<223> OTHER INFORMATION: Recombinant

<400> SEQUENCE: 51

```
aaggccttgg tactgtactc gacgcgggac ggccagaccc acgcaattgc ttcatacatc    60
gcctcctgca tgaaggagaa ggccgaatgc gacgtgatcg acctcaccca cggggagcac   120
gtgaacctca cccaatacga tcaggtgcta atcggtgcga gtattcgtta cggccacttc   180
aacgccgtgc ttgacaagtt catcaagaga aacgtggatc agctgaacaa catgccaagc   240
gcgttcttct gcgtaaacct cacagcaagg aagcccgaga agcgtactcc ccagacaaac   300
ccttatgtcc gaaaattctt gcttgctacc ccctggcagc ccgcgttgtg cggagtgttc   360
gcagggcccc ttcggtaccc gcgataccgg tggatcgaca aggtgatgat ccagctaata   420
atgcggatga ctgggggaga gacagacacg agcaaggagg tcgagtacac ggattgggag   480
caggttaaga agttcgcgga ggattttgca aagctatagt acaagaaggc cctctag     537
```

<210> SEQ ID NO 52
<211> LENGTH: 534
<212> TYPE: DNA
<213> ORGANISM: Artificial Sequence

```
<220> FEATURE:
<223> OTHER INFORMATION: Recombinant

<400> SEQUENCE: 52
aaggccttga tcctgttctc tacacgcgac ggacagacac agaagatcgc atctgccatc    60
gctgatgaga taaaggggca gcaatcgtgc gacgtgatta acatacagga tgccaaaacc   120
ctcgactggc agcagtacga ccgggtactc atcggcgcct ccattcgtta cgggcatttc   180
cagcccgttg tgaatgagtt tgtcaagcac aacctcttgg ccctacagca gagagtttcc   240
ggattcttct ccgtgaactt gacagcccga aagccagaga gcggagccc cgagactaac    300
gcttatacag tcaaattctt ggcgcagtca ccctggcaac cggactgctg cgctgttttt   360
gcgggggccc tgtactaccc acggtaccgg tggttcgata gggtgatgat acagttcata   420
atgcgaatga cgggggggga gaccgacgca tcgaaagagg tggagtacac tgactggcag   480
caggtgcagc ggttcgcgcg agacttcgcg cagttaccgg gtaagtccta ctga         534

<210> SEQ ID NO 53
<211> LENGTH: 540
<212> TYPE: DNA
<213> ORGANISM: Artificial Sequence
<220> FEATURE:
<223> OTHER INFORMATION: Recombinant

<400> SEQUENCE: 53
aagaccctaa tactgttctc tacccgcgac gggcagacaa gggagatcgc cgcgttcctt    60
gcctcggagc tgaaggagca ggggatttac gctgacgtca taaaccttaa ccggacggag   120
gagatagctt ggcaggagta tgatagagtc gtaatcgggg cgtcgatccg atacgggcat   180
ttccaccctg ctgtcgaccg cttcgtgaag aagcacacag agacactcaa ctcactgccc   240
ggcgcctttt tctctgtaaa ccttgttgcc cggaaagccg agaagagaac gccgcagacg   300
aactcataca ccaggaagtt cctattaaac agcccgtgga agccagcggc ctgcgcggtc   360
tttgctgggg ccctccgcta ccctagatac cgctggtacg acaggttcat gatacgactg   420
attatgaaaa tgacaggcgg ggagacggat acccgaaagg aggtagtcta cactgactgg   480
tcgcagatcg cgtcgtttgc cagagagata gtccagttga ccaggtcatc gcgcttgtga   540

<210> SEQ ID NO 54
<211> LENGTH: 540
<212> TYPE: DNA
<213> ORGANISM: Artificial Sequence
<220> FEATURE:
<223> OTHER INFORMATION: Recombinant

<400> SEQUENCE: 54
atgaaggcgc tcgtgctcta cagcacacgc gacggccaga tcatgcgat cgcctcttac     60
atcgcgtcct gtatgaagga gaaggccgag tgcgacgtca tcgatctcac gcacggggag   120
cacgtgaatc ttacgcagta cgaccaagtg ctgataggcg cctctatccg ttacggccat   180
tttaacgccg tcctcgacaa attcatcaag cgcaatgtag accagctgaa caacatgccc   240
tccgcgttct tttgcgtgaa cctgacggct cggaagcctg agaagcgaac acctcagacc   300
aacccatacg tgcggaaatt cctactcgca acgccatggc agcccgccct gtgcggggtt   360
ttcgcagggg cgctacgcta tccgcgttac cgctggatcg ataaggtgat gatccagcta   420
ataatgcgca tgaccggcgg cgagacagac acatcgaagg aagtcgaata cacagactgg   480
gaacaggtga agaagtttgc agaggatttc gccaagctct catacaaaaa ggcattgtga   540
```

<210> SEQ ID NO 55
<211> LENGTH: 537
<212> TYPE: DNA
<213> ORGANISM: Artificial Sequence
<220> FEATURE:
<223> OTHER INFORMATION: Recombinant

<400> SEQUENCE: 55

```
atgaaggcgc ttatactgtt ctcgacacgc gacggtcaga cgcagaaaat cgcctcagcc    60
atcgccgacg agatcaaggg ccagcagagc tgcgatgtga tcaatattca ggacgccaaa   120
actctcgact ggcagcagta tgaccgcgtg ctcattggcg catcaatccg ctacgggcat   180
ttccagccag tcgtcaatga gtttgtgaaa cataacctct ggcattgca gcagcgggtg    240
tctggcttct ctccgtgaa ccttacagct agaaaaccag agaagcgtc gcccgagact     300
aacgcctaca ccgttaagtt ccttgcgcag tcaccgtggc agcctgattg ctgcgcggtc   360
ttcgccgggg cactgtacta ccctcgatac cggtggtttg ataggtaat gatccagttc    420
ataatgcgca tgaccggtgg ggagaccgac gcaagtaaaa agttgagta cacggattgg    480
cagcaggtgc aaaggttcgc acgcgacttc gcgcagctcc cgggcaagtc ttactga     537
```

<210> SEQ ID NO 56
<211> LENGTH: 534
<212> TYPE: DNA
<213> ORGANISM: Artificial Sequence
<220> FEATURE:
<223> OTHER INFORMATION: Recombinant

<400> SEQUENCE: 56

```
atgaaagccc tgatcctcta ttccaccagg gacggccaga cccgcaagat agcctcctcc    60
atcgctgatg tcatccgcca gcagcagcag tgcgacgttt taaacattaa ggacgcttca   120
ctgcctgatt gggcccagta tgaccgcgtc ctgatcggcg cgtcgattcg gtacggccac   180
ttccagcctg tggttgacaa gttcgtcaag cagcacctgc atgagctgca gcagcgaact   240
agcgggttct tcagtgtgaa cctgacagct agaaagcccg aaaagagatc cccagaaacc   300
aacgcctata cgcagaaatt ccttgctcac tcacccctggc agcctgactg ttgtgccgtc   360
ttcgcgggcg ccttgtacta tccccgctac cgctggttcg ataggggtgat gatccagctg   420
attatgagaa tgacgggagg ggagaccgat tcgaccaagg aggtagagta cactgactgg   480
caacaggtgt caactttcgc aaacgacttc gcacaactac ccggtaagtc ttga         534
```

<210> SEQ ID NO 57
<211> LENGTH: 546
<212> TYPE: DNA
<213> ORGANISM: Artificial Sequence
<220> FEATURE:
<223> OTHER INFORMATION: Recombinant

<400> SEQUENCE: 57

```
atgaaaaccc taatactgtt ctcgacccgc gacggccaga cgcgtgagat tgcgagctac    60
ctggcctccg agctcaagga gctggggatc caagccgatg tcgcgaacgt gcaccgcatt   120
gaggagccgc agtgggagaa ttacgatcgc gttgtgatag ggccagcat ccgctatggc    180
cactaccact cggcctttca ggagtttgta agaaacacg ccacaagatt aaactccatg    240
cctagcgcct tctactccgt caaccttgtc gcgcgcaagc cggagaagcg gacacctcag   300
acgaactcct acgcgcggaa gttcctgatg aacagccagt ggcggccgga cagatgtgct   360
gttattgcgg gagccctgag atacccgagg taccggtggt acgataggtt tatgattaaa   420
```

| | |
|---|---|
| cttattatga agatgtctgg tggggagact gacaccagga aggaggtggt atatacagac | 480 |
| tgggagcagg tcgccaattt cgctcgggaa atcgcgcatc tgacagacaa gcctacactg | 540 |
| aagtag | 546 |

<210> SEQ ID NO 58
<211> LENGTH: 537
<212> TYPE: DNA
<213> ORGANISM: Artificial Sequence
<220> FEATURE:
<223> OTHER INFORMATION: Recombinant

<400> SEQUENCE: 58

| | |
|---|---|
| atgaaggccc tgatcctctt tagctctagg gagggccaga cccgcgagat cgcgtcatat | 60 |
| atcgcgaatt ccataaagga ggagatggag tgcgatgtgt taacatcct tagggtggag | 120 |
| caaatagact ggtctcagta tgaccgtgtg ctcatagggg ggagcatcca ctacggccac | 180 |
| tttcacccgg ccgtggcgaa attcgtcaag cgacacctcc acgagcttca gcagcgctcc | 240 |
| tcagggttct tctgcgtcaa cctgacagca agaaaggcag ataaacgcac cccgcagacg | 300 |
| aacgcctaca tgaggaagtt ccttctgcag tctccttggc agcccgattg ctgcgcggtg | 360 |
| ttcgccggtg cactgcgcta tacgcgctat agatggtttg atagagtcat gattcagctc | 420 |
| atcatgcgga tgaccggcgg ggaaacggat actagtaagg aggtggagta cacggactgg | 480 |
| acccaggtgg cacgtttcgc ccaggagttt gcacatcttc ctgggaagac ccaatga | 537 |

<210> SEQ ID NO 59
<211> LENGTH: 540
<212> TYPE: DNA
<213> ORGANISM: Artificial Sequence
<220> FEATURE:
<223> OTHER INFORMATION: Recombinant

<400> SEQUENCE: 59

| | |
|---|---|
| atgaaggcgc taattgtgtt cagctccagg gatggccaga cgagggctat agcatcctat | 60 |
| atcgccaata ccttgaaagg aacgctcgag tgtgacgtgg tcaacgtctt gaacgccaat | 120 |
| gacattgacc tttcccagta cgaccgagtt gccataggcg cgtcgatccg ctacgggcga | 180 |
| tttcaccctg cagtcaacca gtttatacgg aagcatttga cctcgctgca gcagctcccg | 240 |
| tcagccttct tctctgtgaa tttaaccgcg cggaagcctg agaaacggac gatccaaaca | 300 |
| aacgcctata cccgaaagtt cctcctgaac agcccatggc agccagacct gtgctgtgtc | 360 |
| ttcgccggcg cgttgcggta tccccgctac aggtggttcg atagagtgat gatccagctc | 420 |
| atcatgagga tcaccggggg agagaccgat agtaccaagg agatcgagta cacggactgg | 480 |
| cagcaggtgg ctcgcttcgc ccaggacttc gctcagttgg ccgcaaagaa tccagcataa | 540 |

<210> SEQ ID NO 60
<211> LENGTH: 540
<212> TYPE: DNA
<213> ORGANISM: Artificial Sequence
<220> FEATURE:
<223> OTHER INFORMATION: Recombinant

<400> SEQUENCE: 60

| | |
|---|---|
| atgaagacac tgatcctgtt ctcgactcga gatggccaga ctcataaaat tgcgcgccac | 60 |
| attgcggggg tcctggagga gcagggcaaa gcgtgcgagc tcgtggactt actccagccc | 120 |
| ggggagccgg actggagcac ggtggagtgc gtcgttctgg gcgcttccat acgttacggg | 180 |

```
catttccaca aaagtttcat ccggttcgtc aacacccacg ctcaacggct gaacaacatg    240
cctggcgcgc tattcactgt taacttagtg gctcgtaagc ccgagaagca gtctccgcag    300
actaactcct acacaaggaa atttctagca gcaagcccat ggcaaccgca gcggtgccag    360
gtgttcgctg gagctctgcg ctatcctagg tacagttggt acgacagaat gatgatacgg    420
ttgattatga agatggcagg cggggagacg gacaccagga aagaggtcga atacactgac    480
tggcaatcag tcactcggtt tgctagagag atcgcgcaat taccaggtga gacgcggtaa    540
```

<210> SEQ ID NO 61
<211> LENGTH: 537
<212> TYPE: DNA
<213> ORGANISM: Artificial Sequence
<220> FEATURE:
<223> OTHER INFORMATION: Recombinant

<400> SEQUENCE: 61

```
atgaaggctc tcatactgtt cagctcgaga gacgggcaga cccagctgat cgcctcctcc    60
atagcaaagg agctagaggg caagcaagcc tgcgacgtgc tcaatattct cgacacaacc    120
aacgtggagt ggactcagta cgacagagtc ctaatcggcg cgtccatcag atacggccac    180
ttccatcccg ccgtcgctga attcgtgaaa cgccaccagc gtgagctcca gcagcgcagc    240
agcggcttct tcagcgtgaa tcttactgcg agaaagccgg aaaagcggag tcccgagact    300
aacgcttata cggcaaagtt cctcaaccaa tctccctggc aaccagactg ctgtgccgtg    360
ttcgctgggg cactgaggta tccgcgctat cggtggttcg atagaatcat gatacagctg    420
ataatgcgta tgactggtgg ggagacggat tccagtaaag aggtagagta tactgattgg    480
cagcaggtca ctaggttcgc gcaggagttt gctaggctgc cgggcaagac atcctga       537
```

<210> SEQ ID NO 62
<211> LENGTH: 543
<212> TYPE: DNA
<213> ORGANISM: Artificial Sequence
<220> FEATURE:
<223> OTHER INFORMATION: Recombinant

<400> SEQUENCE: 62

```
atgaaaacct taatcttgtt cagcacccgc gacggccaga cgcgtgaaat cgcagcgttc    60
ctcgcttcgg agctcaagga acagggaatt tacgccgacg tcattaacct aaaccgtacc    120
gaagagattg cgtggcagga gtatgaccgc gtggtgattg gcgcttctat ccgctatggc    180
cacttccacc cggctgttga ccggttcgtg aagaagcaca cggagacctt gaactcactg    240
ccgggggcat tctttagcgt aaatctggtg gcgcgcaagg ccgagaagcg cacccccag     300 acgaacagct acacccgcaa attttttactt aactccccat ggaaacctgc ggcctgcgca    360
gtgttcgcag gagctctccg ctatcctcgc tatcgatggt acgatcggtt catgattcgg    420
ctgattatga aaatgacggg cggcgagacg gatacgcgaa aggaagttgt ctacactgac    480
tggtcccagg tggcctcgtt tgcaagggag atcgtacagc tcactcgatc tagtaggctc    540
tga                                                                   543
```

<210> SEQ ID NO 63
<211> LENGTH: 534
<212> TYPE: DNA
<213> ORGANISM: Artificial Sequence
<220> FEATURE:
<223> OTHER INFORMATION: Recombinant

<400> SEQUENCE: 63

```
atgaagattc tcatcttatt ttccacccga gacggccaaa cccgcgagat tgcggcgtcc      60
ctcgcctccg agttgaagga gcaggcgttt gatgtggatg tggtcaacct ccaccgcgca     120
gaaaacatag cgtgggagga gtacgatggg gtcgtcatcg gagcgtcaat ccgctacgga     180
catttccact caacgctgaa ttcatttgtg aagaagcacc aacaagcgct caagaagctg     240
cccggagcat tctacagcgt caacctcgtg gctcggaagc cggaaaagcg cacccgcaa      300 acaaacagct acacacgcaa gtttctgctc gactcgccct ggcaacccga cctgagtgcc     360
gttttcgccg gggcactgcg ctatccccgt tacaactggt acgatcgcat aatgattcga     420
ctgatcatga agattacagg cggggaaacc gatactcgga aggaggtggt gtatacagac     480
tggcagcagg ttacccactt cgcccacgag atcgtccagc tcgttcgtaa gtga           534
```

METHODS AND COMPOSITIONS FOR PPO HERBICIDE TOLERANCE IN PLANTS

CROSS-REFERENCE TO RELATED APPLICATIONS

This application is a divisional of U.S. application Ser. No. 15/224,276, filed Jul. 29, 2016 (pending), which application claims the benefit of priority of U.S. Provisional Application Ser. No. 62/200,428 filed Aug. 3, 2015, the disclosures of which are hereby incorporated by reference in their entirety.

INCORPORATION OF SEQUENCE LISTING

The sequence listing that is contained in the file named MONS383US_ST25.txt, which is 71,195 bytes (measured in MS-WINDOWS) and created on Jun. 27, 2016, is filed herewith by electronic submission and incorporated herein by reference.

BACKGROUND

Field of the Invention

The present invention relates to the field of biotechnology. More specifically, the invention relates to recombinant DNA molecules encoding enzymes that provide tolerance to herbicides that inhibit protoporphyrinogen oxidase.

Related Art

Agricultural crop production often utilizes transgenic traits created using the methods of biotechnology. A heterologous gene, also known as a transgene, can be introduced into a plant to produce a transgenic trait. Expression of the transgene in the plant confers a trait, such as herbicide tolerance, on the plant. Examples of transgenic herbicide tolerance traits include glyphosate tolerance, glufosinate tolerance, and dicamba tolerance. With the increase of weed species resistant to the commonly used herbicides, new herbicide tolerance traits are needed in the field. Herbicides of particular interest include herbicides that inhibit protoporphyrinogen oxidase (PPO), referred to as PPO herbicides. PPO herbicides provide control of a spectrum of herbicide-resistant weeds, thus making a trait conferring tolerance to these herbicides particularly useful in a cropping system combined with one or more other herbicide-tolerance trait(s).

Protoporphyrinogen oxidase functions in both chlorophyll and heme biosynthesis pathways where it converts protoporphyrinogen IX to protoporphyrin IX. Following production of protoporphyrin IX, the chlorophyll and heme biosynthetic pathways diverge with different metal ions being incorporated (iron for heme and magnesium for chlorophyll). Segments of this pathway are conserved across prokaryotes and eukaryotes, and many of the PPO enzymes found across prokaryotes and eukaryotes are relatively similar. Some prokaryotes (e.g., cyanobacteria) use this pathway for chlorophyll and heme production while other prokaryotes (e.g., *Escherichia coli*) use this pathway for heme production.

Herbicide-insensitive protoporphyrinogen oxidases ("iPPOs") have been isolated from a number of prokaryotes and eukaryotes. On a structural basis, it is believed that there are at least three distinct subclasses of PPO enzymes: HemY (Hans son and Hederstedt, "Cloning and characterization of the *Bacillus subtilis* hemEHY gene cluster, which encodes protoheme IX biosynthetic enzymes" *Journal of Bacteriology* 174(24):8081-8093 (1992)), HemG (Sasarman, et al., "Mapping of a new hem gene in *Escherichia coli* K12" *Microbiology* 113:297-303 (1979)), and HemJ (Boynton, et al., "Discovery of a gene involved in a third bacterial protoporphyrinogen oxidase activity through comparative genomic analysis and functional complementation" *Applied and Environmental Microbiology* 77(14):4795-4801 (2011)). This invention provides novel recombinant iPPOs that are members of the HemG family. Despite twenty years of research and the number of iPPOs identified to date, a transgenic crop plant comprising a recombinant iPPO has yet to be commercialized. A strong weed control platform depends, in part, on continued development of herbicide tolerance trait packages. Identifying and utilizing iPPOs to create transgenic crop traits therefore represents an advance to agriculture.

SUMMARY OF THE INVENTION

In one aspect, the invention provides a recombinant DNA molecule comprising a heterologous promoter operably linked to a nucleic acid sequence encoding a polypeptide that has at least 85% sequence identity to a polypeptide sequence chosen from SEQ ID NOs:1-20, wherein the polypeptide has herbicide-insensitive protoporphyrinogen oxidase activity. In certain embodiments, the polypeptide has at least about 85% sequence identity, at least about 90% sequence identity, at least 95% sequence identity, at least 96% sequence identity, at least 97% sequence identity, at least 98% sequence identity, or at least 99% sequence identity to a polypeptide sequence chosen from among SEQ ID NOs:1-20 and has herbicide-insensitive protoporphyrinogen oxidase activity. In some embodiments there is provided a recombinant DNA molecule, wherein the nucleic acid sequence is selected from the group consisting of SEQ ID NOs:22-63. In particular embodiments the recombinant DNA molecule encodes a polypeptide comprising an amino acid sequence selected from the group consisting of SEQ ID NOs:1-20. A recombinant polypeptide that comprises at least 85% sequence identity to the full length of an amino acid sequence chosen from among SEQ ID NOs:1-20, wherein the polypeptide has herbicide-insensitive protoporphyrinogen oxidase activity is therefore provided by the invention.

In certain embodiments a heterologous promoter, for instance, a promoter functional in a plant cell, is operably linked to the nucleic acid sequence encoding a polypeptide that has at least 85% sequence identity to a polypeptide sequence of the invention, for instance a polypeptide sequence chosen from SEQ ID NOs:1-20, wherein the polypeptide has herbicide-insensitive protoporphyrinogen oxidase activity. Such a resulting DNA molecule may further comprise a targeting sequence that functions to localize the polypeptide within a cell.

In one aspect, the invention provides a DNA construct comprising a recombinant DNA molecule of the invention. In one embodiment, such a DNA construct comprises, in operable linkage to a nucleic acid sequence of the invention, a targeting sequence that functions to localize the polypeptide within a cell. The DNA molecule may be present in the genome of a transgenic plant, seed, or cell. In certain embodiments, the polypeptide confers herbicide tolerance to the cell, plant, seed, or plant part.

Another aspect of the invention provides a transgenic plant, seed, cell, or plant part comprising a recombinant DNA molecule of the invention or a recombinant polypeptide of the invention. The transgenic plant, seed, cell, or plant part may thus comprise, i.e. display, tolerance to at least one PPO herbicide. In some embodiments the transgenic plant, seed, cell, or plant part comprises an additional transgenic herbicide tolerance trait.

Another aspect of the invention provides a method for conferring herbicide tolerance to a plant, seed, cell, or plant part comprising: heterologously expressing a recombinant polypeptide of the invention in the plant, seed, cell, or plant part. In some embodiments of the method, the plant, seed, cell, or plant part comprises protoporphyrinogen oxidase activity conferred by the recombinant polypeptide. In some embodiments the herbicide tolerance is to at least one PPO herbicide selected from the group consisting of acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil and S-3100.

Another aspect of the invention relates to a method of plant transformation, comprising the steps of: a) introducing a recombinant DNA molecule of the invention into a plant cell; and b) regenerating a transgenic plant therefrom that comprises the recombinant DNA molecule. The method may further comprise the step of selecting a plant that is tolerant to at least one PPO herbicide. The method may also further comprise a step of crossing the regenerated plant with itself or with a second plant and collecting seed from the cross.

Yet another aspect of the invention provides a method for controlling weeds in a plant growth area, comprising contacting a plant growth area comprising the transgenic plant or seed with at least one PPO herbicide, wherein the transgenic plant or seed is tolerant to the PPO herbicide and wherein weeds are controlled in the plant growth area.

Also provided is a method of identifying a nucleotide sequence encoding a protein having protoporphyrinogen oxidase activity, the method comprising: a) transforming an *E. coli* strain having a gene knockout for the native *E. coli* PPO enzyme with a bacterial expression vector comprising a recombinant DNA molecule encoding a candidate herbicide tolerance protein; and b) growing said transformed *E. coli* using a heme-free bacterial medium, wherein growth using said bacterial medium identifies a protein having protoporphyrinogen oxidase activity.

Further provided by the invention is a method of identifying a nucleotide sequence encoding a protein having herbicide-insensitive protoporphyrinogen oxidase activity, the method comprising: a) transforming an *E. coli* strain having a gene knockout for the native *E. coli* PPO enzyme with a bacterial expression vector comprising a recombinant DNA molecule encoding a recombinant protein; and b) growing said transformed *E. coli* using a bacterial medium containing at least one PPO herbicide, wherein growth of bacteria identifies a protein having herbicide-insensitive protoporphyrinogen oxidase activity.

Another aspect of the invention relates to a method of screening for a herbicide tolerance gene comprising: a) expressing a recombinant DNA molecule of the invention in a plant cell; and b) identifying a plant cell that displays tolerance to a PPO herbicide.

Further, the invention provides methods of screening for a herbicide tolerance gene comprising: a) expressing a recombinant DNA molecule of the invention in a bacterial cell lacking HemG, wherein the bacterial cell is grown in a heme-free medium in the presence of a PPO herbicide; and b) identifying a bacterial cell that displays tolerance to a PPO herbicide.

In another aspect, the invention provides a method of producing a plant tolerant to a PPO herbicide and at least one other herbicide comprising: a) obtaining a plant comprising a recombinant DNA molecule of the invention; b) crossing the transgenic plant with a second plant comprising tolerance to the at least one other herbicide, and c) selecting a progeny plant resulting from said crossing that comprises tolerance to a PPO herbicide and the at least one other herbicide is another aspect of the invention.

The invention also provides, in another aspect, a method for reducing the development of herbicide tolerant weeds comprising: a) cultivating in a crop growing environment a plant of the present invention that comprises tolerance to a PPO herbicide, for instance by comprising a DNA molecule of the present invention, and comprises tolerance to at least one other herbicide; and b) applying a PPO herbicide and at least one other herbicide to the crop growing environment, wherein the crop plant is tolerant to the PPO herbicide and the at least one other herbicide. In certain embodiments of the method, the PPO herbicide may be selected from the group consisting of acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil and S-3100. In some embodiments of the method, the at least one other herbicide is selected from the group consisting of: an ACCase inhibitor, an ALS inhibitor, an EPSPS inhibitor, a synthetic auxin, a photosynthesis inhibitor, a glutamine synthesis inhibitor, a HPPD inhibitor, a PPO inhibitor, and a long-chain fatty acid inhibitor. In particular embodiments, the ACCase inhibitor is an aryloxyphenoxy propionate or a cyclohexanedione; the ALS inhibitor is a sulfonylurea, imidazolinone, triazoloyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthesis inhibitor is glufosinate; the HPPD inhibitor is an isoxazole, a pyrazolone, or a triketone; the PPO inhibitor is a diphenylether, a N-phenylphthalimide, an aryl triazinone, or a pyrimidinedione; or the long-chain fatty acid inhibitor is a chloroacetamide, an oxyacetamide, or a pyrazole.

BRIEF DESCRIPTION OF THE DRAWINGS

FIG. 1. Alignment of H_N90, H_N20, H_N60, H_N10, H_N30, H_N40, H_N50, H_N70, H_N100, and H_N110 protein sequences (SEQ ID NOs:1-10), with consensus positions shown below.

BRIEF DESCRIPTION OF THE SEQUENCES

Figure 2:
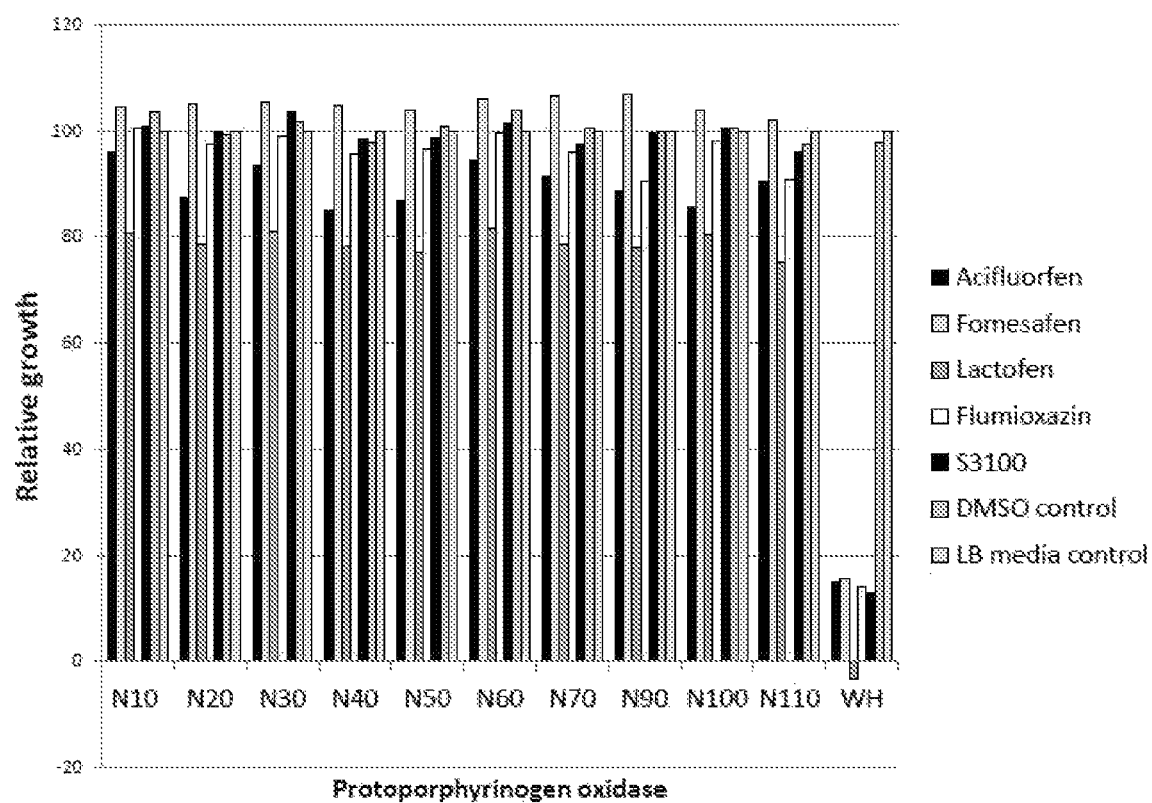
FIG. 2. Assay results from PPO bacterial screening system with PPO herbicides measured at 8 hours of growth of *E. coli* containing the tested iPPO.

SEQ ID NO:1 is the amino acid sequence of H_N90.
SEQ ID NO:2 is the amino acid sequence of H_N20.
SEQ ID NO:3 is the amino acid sequence of H_N60.
SEQ ID NO:4 is the amino acid sequence of H_N10, which is the *E. coli* wild-type HemG protoporphyrinogen oxidase (NCBI GenBank Accession No. WP_021498199).
SEQ ID NO:5 is the amino acid sequence of H_N30.
SEQ ID NO:6 is the amino acid sequence of H_N40.
SEQ ID NO:7 is the amino acid sequence of H_N50.
SEQ ID NO:8 is the amino acid sequence of H_N70.
SEQ ID NO:9 is the amino acid sequence of H_N100.
SEQ ID NO:10 is the amino acid sequence of H_N110.

SEQ ID NO:11 through SEQ ID NO:17 are amino acid sequences lacking the start methonine corresponding to SEQ ID NO:1, 2, 4, 5, 6, 7, and 9, respectively.

SEQ ID NO:18 and SEQ ID NO:19 are amino acid variants of SEQ ID NO:11.

SEQ ID NO:20 is an amino acid variant of SEQ ID NO:17.

SEQ ID NO:21 is the amino acid sequence of the WH, which is the wild-type protoporphyrinogen oxidase from *Amaranthus tuberculatus* (waterhemp).

SEQ ID NO:22 through SEQ ID NO:31 are nucleotide sequences encoding SEQ ID NO.: 1 through SEQ ID NO:10, respectively, codon optimized for *E. coli* expression.

SEQ ID NO:32 through SEQ ID NO:41 are the nucleotide sequences encoding SEQ ID NO.: 1 through SEQ ID NO:10, respectively, codon optimized for dicot expression.

SEQ ID NO:42 through SEQ ID NO:48 are the nucleotide sequences encoding SEQ ID NO:11 through SEQ ID NO:17, respectively, codon optimized for dicot expression.

SEQ ID NO:49 and SEQ ID NO:52 are nucleotide variants of SEQ ID NO:11 and SEQ ID NO:12, respectively.

SEQ ID NOs:50, 51 and 53 are nucleotide sequences encoding SEQ ID NOs:18, 19, and 20.

SEQ ID NO:54 through SEQ ID NO:63 are the nucleotide sequences encoding SEQ ID NO.: 1 through SEQ ID NO:10, respectively, codon optimized for monocot expression.

DETAILED DESCRIPTION

The following descriptions and definitions are provided to better define the invention and to guide those of ordinary skill in the art in the practice of the invention. Unless otherwise noted, terms are to be understood according to conventional usage by those of ordinary skill in the relevant art.

The invention provides novel, recombinant DNA molecules and proteins that encode herbicide-insensitive protoporphyrinogen oxidases (iPPOs). For instance, the invention provides in one embodiment vectors and expression cassettes encoding microbially derived iPPOs for expression in cells and plants. Methods for producing cells and plants tolerant to PPO herbicides are also provided. The invention further provides methods and compositions for using protein engineering and bioinformatic tools to obtain and improve iPPOs.

In specific aspects, the invention provides recombinant DNA molecules and proteins. As used herein, the term "recombinant" refers to a non-naturally occurring DNA, protein, cell, seed, or organism that is the result of genetic engineering and as such would not normally be found in nature. A "recombinant DNA molecule" is a DNA molecule comprising a DNA sequence that does not naturally occur in nature and as such is the result of human intervention, such as a DNA molecule comprised of at least two DNA molecules heterologous to each other. An example of a recombinant DNA molecule is a DNA molecule provided herein encoding herbicide-insensitive protoporphyrinogen oxidase operably linked to a heterologous regulatory or other element, such as a heterologous promoter. A "recombinant protein" is a protein comprising an amino acid sequence that does not naturally occur and as such is the result of human intervention, such as an engineered protein or a chimeric protein. A recombinant cell, seed, or organism is a cell, seed, or organism comprising transgenic DNA, for example a transgenic cell, seed, plant, or plant part comprising a recombinant DNA molecule and therefore produced as a result of plant transformation.

As used herein, the term "genetic engineering" refers to the creation of a non-natural DNA, protein, or organism that would not normally be found in nature and therefore entails applying human intervention. Genetic engineering can be used to produce an engineered DNA, protein, or organism that was conceived of and created in the laboratory using one or more of the techniques of biotechnology such as molecular biology, protein biochemistry, bacterial transformation, and plant transformation. For example, genetic engineering can be used to create a chimeric gene comprising at least two DNA molecules heterologous to each other using one or more of the techniques of molecular biology, such as gene cloning, DNA ligation, and DNA synthesis. A chimeric gene may consist of two or more heterologous DNA molecules that are operably linked, such as a protein-coding sequence operably linked to a gene expression element such as a transit peptide-coding sequence or a heterologous promoter. Genetic engineering can be used to create an engineered protein whose polypeptide sequence was created using one or more of the techniques of protein engineering, such as protein design using site-directed mutagenesis and directed evolution using random mutagenesis and DNA shuffling. An engineered protein may have one or more deletions, insertions, or substitutions relative to the coding sequence of the wild-type protein and each deletion, insertion, or substitution may consist of one or more amino acids. In another embodiment, an engineered protein may consist of two heterologous peptides that are operably linked, such as an enzyme operably linked to a transit peptide.

As used herein, "herbicide-insensitive" means the ability of a protoporphyrinogen oxidase (PPO) to maintain at least some of its enzymatic activity in the presence of one or more PPO herbicide(s). Enzymatic activity of a protoporphyrinogen oxidase can be measured by any means known in the art, for example, by an enzymatic assay in which the production of the product of protoporphyrinogen oxidase or the consumption of the substrate of protoporphyrinogen oxidase in the presence of one or more PPO herbicide(s) is measured via fluorescence, high performance liquid chromatography (HPLC), or mass spectrometry (MS). Another example of an assay for measuring enzymatic activity of a protoporphyrinogen oxidase is a bacterial assay, such as the growth assays described herein, whereby a recombinant protoporphyrinogen oxidase is expressed in a bacterial cell otherwise lacking PPO activity and the ability of the recombinant protoporphyrinogen oxidase to complement this knockout phenotype is measured. Herbicide-insensitivity may be complete or partial insensitivity to a particular herbicide, and may be expressed as a percent (%) tolerance or insensitivity to a particular PPO herbicide. As used herein, an "herbicide-insensitive protoporphyrinogen oxidase" or "iPPO" exhibits herbicide-insensitivity in the presence of one or more PPO herbicide(s).

As used herein, a "hemG knockout strain" means an organism or cell of an organism, such as *E. coli*, that lacks HemG activity to the extent that it is unable to grow on heme-free growth medium, or such that its growth is detectably impaired in the absence of heme relative to an otherwise isogenic strain comprising a functional HemG. A hemG knockout strain of, for instance, *E. coli* may be prepared in view of knowledge in the art, for instance in view of the *E. coli* hemG sequence (Ecogene Accession No. EG11485; Sasarman et al., "Nucleotide sequence of the hemG gene involved in the protoporphyrinogen oxidase activity of *Escherichia coli* K12" *Can J Microbiol* 39:1155-1161, 1993).

As used herein, the term "transgene" refers to a DNA molecule artificially incorporated into an organism's genome because of human intervention, such as a plant transformation method. As used herein, the term "transgenic" means comprising a transgene, for example a "transgenic plant" refers to a plant comprising a transgene in its genome and a "transgenic trait" refers to a characteristic or phenotype conveyed or conferred by the presence of a transgene incorporated into the plant genome. Because of such genomic alteration, the transgenic plant is something distinctly different from the related wild-type plant and the transgenic trait is a trait not naturally found in the wild-type plant. Transgenic plants of the invention comprise the recombinant DNA molecules and engineered proteins provided by the invention.

As used herein, the term "heterologous" refers to the relationship between two or more items derived from different sources and thus not normally associated in nature. For example, a protein-coding recombinant DNA molecule is heterologous with respect to an operably linked promoter if such a combination is not normally found in nature. In addition, a particular recombinant DNA molecule may be heterologous with respect to a cell, seed, or organism into which it is inserted when it would not naturally occur in that particular cell, seed, or organism.

As used herein, the term "isolated" refers to at least partially separating a molecule from other molecules typically associated with it in its natural state. In one embodiment, the term "isolated" refers to a DNA molecule that is separated from the nucleic acids that normally flank the DNA molecule in its natural state. For example, a DNA molecule encoding a protein that is naturally present in a bacterium would be an isolated DNA molecule if it was not within the DNA of the bacterium from which the DNA molecule encoding the protein is naturally found. Thus, a DNA molecule fused to or operably linked to one or more other DNA molecule(s) with which it would not be associated in nature, for example as the result of recombinant DNA or plant transformation techniques, is considered isolated herein. Such molecules are considered isolated even when integrated into the chromosome of a host cell or present in a nucleic acid solution with other DNA molecules.

As used herein, the term "protein-coding DNA molecule" refers to a DNA molecule comprising a nucleotide sequence that encodes a protein. A "protein-coding sequence" means a DNA sequence that encodes a protein. A "sequence" means a sequential arrangement of nucleotides or amino acids. The boundaries of a protein-coding sequence may be determined by a translation start codon at the 5'-terminus and a translation stop codon at the 3'-terminus. A protein-coding molecule may comprise a DNA sequence encoding a protein sequence. As used herein, "transgene expression", "expressing a transgene", "protein expression", and "expressing a protein" mean the production of a protein through the process of transcribing a DNA molecule into messenger RNA (mRNA) and translating the mRNA into polypeptide chains, which are ultimately folded into proteins. A protein-coding DNA molecule may be operably linked to a heterologous promoter in a DNA construct for use in expressing the protein in a cell transformed with the recombinant DNA molecule. As used herein, "operably linked" means two DNA molecules linked in manner so that one may affect the function of the other. Operably-linked DNA molecules may be part of a single contiguous molecule and may or may not be adjacent. For example, a promoter is operably linked with a protein-coding DNA molecule in a DNA construct where the two DNA molecules are so arranged that the promoter may affect the expression of the transgene.

As used herein, a "DNA construct" is a recombinant DNA molecule comprising two or more heterologous DNA sequences. DNA constructs are useful for transgene expression and may be comprised in vectors and plasmids. DNA constructs may be used in vectors for the purpose of transformation, that is the introduction of heterologous DNA into a host cell, to produce transgenic plants and cells, and as such may also be contained in the plastid DNA or genomic DNA of a transgenic plant, seed, cell, or plant part. As used herein, a "vector" means any recombinant DNA molecule that may be used for the purpose of bacterial or plant transformation. Recombinant DNA molecules as set forth in the sequence listing, can, for example, be inserted into a vector as part of a construct having the recombinant DNA molecule operably linked to a gene expression element that functions in a plant to affect expression of the engineered protein encoded by the recombinant DNA molecule. General methods useful for manipulating DNA molecules for making and using recombinant DNA constructs and plant transformation vectors are well known in the art and described in detail in, for example, handbooks and laboratory manuals including MR Green and J Sambrook, "Molecular Cloning: A Laboratory Manual" (Fourth Edition) ISBN: 978-1-936113-42-2, Cold Spring Harbor Laboratory Press, NY (2012). The components for a DNA construct, or a vector comprising a DNA construct, include one or more gene expression elements operably linked to a transcribable DNA sequence, such as the following: a promoter for the expression of an operably linked DNA, an operably linked protein-coding DNA molecule, and an operably linked 3' untranslated region (UTR). Gene expression elements useful in practicing the present invention include, but are not limited to, one or more of the following type of elements: promoter, 5' UTR, enhancer, leader, cis-acting element, intron, targeting sequence, 3' UTR, and one or more selectable marker transgenes.

The DNA constructs of the invention may include a promoter operably linked to a protein-coding DNA molecule provided by the invention, whereby the promoter drives expression of the recombinant protein molecule. Promoters useful in practicing the present invention include those that function in a cell for expression of an operably linked polynucleotide, such as a bacterial or plant promoter. Plant promoters are varied and well known in the art and include, for instance, those that are inducible, viral, synthetic, constitutive, temporally regulated, spatially regulated, and/or spatio-temporally regulated.

In one embodiment of the invention, a DNA construct provided herein includes a targeting sequence that is operably linked to a heterologous nucleic acid encoding a polypeptide molecule that has herbicide-insensitive protoporphyrinogen oxidase activity, whereby the targeting sequence facilitates localizing the polypeptide molecule within the cell. Targeting sequences are known in the art as signal sequences, targeting peptides, localization sequences, and transit peptides. An example of a targeting sequence is a chloroplast transit peptide (CTP), a mitochondrial targeting sequence (MTS), or a dual chloroplast and mitochondrial targeting peptide. By facilitating protein localization within the cell, the targeting sequence may increase the accumulation of recombinant protein, protect the protein from proteolytic degradation, and/or enhance the level of herbicide tolerance, and thereby reduce levels of injury in the transgenic cell, seed, or organism after herbicide application.

CTPs and other targeting molecules that may be used in connection with the present invention are known in the art and include, but are not limited to, the *Arabidopsis thaliana* EPSPS CTP (Klee et al., *Mol Gen Genet.* 210:437-442, 1987), the *Petunia hybrida* EPSPS CTP (della-Cioppa et al., *PNAS* 83:6873-6877, 1986), the maize cab-m7 signal sequence (Becker et al., *Plant Mol Biol.* 20:49-60, 1992; PCT WO 97/41228), a mitochondrial pre-sequence (e.g. Silva Filho et al., *Plant Mol Biol* 30:769-780, 1996), and the pea glutathione reductase signal sequence (Creissen et al., *Plant J.* 8:167-175, 1995; PCT WO 97/41228).

Recombinant DNA molecules of the present invention may be synthesized and modified by methods known in the art, either completely or in part, where it is desirable to provide sequences useful for DNA manipulation (such as restriction enzyme recognition sites or recombination-based cloning sites), plant-preferred sequences (such as plant-codon usage or Kozak consensus sequences), or sequences useful for DNA construct design (such as spacer or linker sequences). The present invention includes recombinant DNA molecules and engineered proteins having at least 70% sequence identity, at least 80% sequence identity, at least 85% sequence identity, at least 90% sequence identity, at least 95% sequence identity, at least 96% sequence identity, at least 97% sequence identity, at least 98% sequence identity, and at least 99% sequence identity to any of the recombinant DNA molecule or polypeptide sequences provided herein, and having herbicide-insensitive protoporphyrinogen oxidase activity. As used herein, the term "percent sequence identity" or "% sequence identity" refers to the percentage of identical nucleotides or amino acids in a linear polynucleotide or polypeptide sequence of a reference ("query") sequence (or its complementary strand) as compared to a test ("subject") sequence (or its complementary strand) when the two sequences are optimally aligned (with appropriate nucleotide or amino acid insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and by computerized implementations of these algorithms such as GAP, BESTFIT, FASTA, and TFASTA available as part of the Sequence Analysis software package of the GCG® Wisconsin Package® (Accelrys Inc., San Diego, Calif.), MEGAlign (DNAStar Inc., 1228 S. Park St., Madison, Wis. 53715), and MUSCLE (version 3.6) (Edgar, "MUSCLE: multiple sequence alignment with high accuracy and high throughput" *Nucleic Acids Research* 32(5):1792-7 (2004)) for instance with default parameters. An "identity fraction" for aligned segments of a test sequence and a reference sequence is the number of identical components that are shared by the two aligned sequences divided by the total number of components in the portion of the reference sequence segment being aligned, that is, the entire reference sequence or a smaller defined part of the reference sequence. Percent sequence identity is represented as the identity fraction multiplied by 100. The comparison of one or more sequences may be to a full-length sequence or a portion thereof, or to a longer sequence.

Engineered proteins may be produced by changing (that is, modifying) a wild-type protein to produce a new protein with modified characteristic(s) e.g. a particular cellular localization pattern, such as targeted to the chloroplast or mitochondria, or a novel combination of useful protein characteristics, such as altered $V_{max}$, $K_m$, $K_i$, $IC_{50}$, substrate specificity, inhibitor/herbicide specificity, substrate selectivity, the ability to interact with other components in the cell such as partner proteins or membranes, and protein stability, among others.

Modifications may be made at specific amino acid positions in a protein and may be a substitution of the amino acid found at that position in nature (that is, in the wild-type protein) with a different amino acid. Engineered proteins provided by the invention thus provide a new protein with one or more altered protein characteristics relative to a similar protein found in nature. In one embodiment of the invention, an engineered protein has altered protein characteristics, such as those that result in decreased sensitivity to one or more herbicides as compared to a similar wild-type protein, or improved ability to confer herbicide tolerance on a transgenic plant expressing the engineered protein to one or more herbicides. In one embodiment, the invention provides an engineered protein, and the recombinant DNA molecule encoding it, comprising at least one amino acid substitution selected from Table 1 and having at least about 70% sequence identity, about 80% sequence identity, about 85% sequence identity, about 90% sequence identity, about 95% sequence identity, about 96% sequence identity, about 97% sequence identity, about 98% sequence identity, and about 99% sequence identity to any of the engineered protein sequences provided herein, including but not limited to SEQ ID NO:1-20. Amino acid mutations may be made as a single amino acid substitution in the protein or in combination with one or more other mutation(s), such as one or more other amino acid substitution(s), deletions, or additions. Mutations may be made by any method known to those of skill in the art.

TABLE 1

Amino Acid Substitutions.

| Residue | Conservative Substitutions | Residue | Conservative Substitutions |
| --- | --- | --- | --- |
| Ala | Ser | Leu | Ile; Val |
| Arg | Lys | Lys | Arg; Gln |
| Asn | Gln; His | Met | Leu; Ile |
| Asp | Glu | Phe | Met; Leu; Tyr |
| Gln | Asn | Ser | Thr; Gly |
| Cys | Ser | Thr | Ser; Val |
| Glu | Asp | Trp | Tyr |
| Gly | Pro | Tyr | Trp; Phe |
| His | Asn; Gln | Val | Ile; Leu |
| Ile | Leu; Val | | |

As used herein, "wild-type" means a naturally occurring similar, but not identical, version. A "wild-type DNA molecule" or "wild-type protein" is a naturally occurring version of the DNA molecule or protein, that is, a version of the DNA molecule or protein pre-existing in nature. An example of a wild-type protein useful for comparison with the engineered proteins provided by the invention is the protoporphyrinogen oxidase from *Arabidopsis thaliana*. A "wild-type plant" is a non-transgenic plant of the same type as the transgenic plant, and as such is genetically distinct from the transgenic plant comprising the herbicide tolerance trait. Examples of a wild-type plant useful for comparison with transgenic maize plants are non-transgenic LH244 maize (ATCC deposit number PTA-1173) and 01DKD2 inbred maize (1294213) (ATCC deposit number PTA-7859). For transgenic soybean plants an exemplary comparative line would be non-transgenic A3555 soy (ATCC deposit number PTA-10207), and for transgenic cotton plants an exemplary comparative line would be non-transgenic Coker 130 (Plant Variety Protection Number 8900252).

Transgenic Plants & Herbicides

One aspect of the invention includes transgenic plant cells, transgenic plant tissues, transgenic plants, and transgenic seeds that comprise the recombinant DNA molecules and engineered proteins provided by the invention. These cells, tissues, plants, and seeds comprising the recombinant DNA molecules and engineered proteins exhibit herbicide tolerance to one or more PPO herbicide(s), and, optionally, tolerance to one or more additional herbicide(s).

Suitable methods for transformation of host plant cells for use with the current invention include virtually any method by which DNA can be introduced into a cell (for example, where a recombinant DNA construct is stably integrated into a plant chromosome) and are well known in the art. An exemplary and widely utilized method for introducing a recombinant DNA construct into plants is the *Agrobacterium* transformation system, which is well known to those of skill in the art. Another exemplary method for introducing a recombinant DNA construct into plants is insertion of a recombinant DNA construct into a plant genome at a predetermined site by methods of site-directed integration. Site-directed integration may be accomplished by any method known in the art, for example, by use of zinc-finger nucleases, engineered or native meganucleases, TALE-endonucleases, or an RNA-guided endonuclease (for example a CRISPR/Cas9 system). Transgenic plants can be regenerated from a transformed plant cell by the methods of plant cell culture. A transgenic plant homozygous with respect to a transgene (that is, two allelic copies of the transgene) can be obtained by self-pollinating (selfing) a transgenic plant that contains a single transgene allele with itself, for example an R0 plant, to produce R1 seed. One fourth of the R1 seed produced will be homozygous with respect to the transgene. Plants grown from germinating R1 seed can be tested for zygosity, using a SNP assay, DNA sequencing, or a thermal amplification assay that allows for the distinction between heterozygotes and homozygotes, referred to as a zygosity assay.

As used herein, a "PPO inhibitor herbicide" or "PPO herbicide" is a chemical that targets and inhibits the enzymatic activity of a protoporphyrinogen oxidase (PPO), which catalyzes the dehydrogenation of protoporphyrinogen IX to form protoporphyrin IX, which is the precursor to heme and chlorophyll. Inhibition of protoporphyrinogen oxidase causes formation of reactive oxygen species, resulting in cell membrane disruption and ultimately the death of susceptible cells. PPO herbicides are well-known in the art and commercially available. Examples of PPO herbicides include, but are not limited to, diphenylethers (such as acifluorfen, its salts and esters, aclonifen, bifenox, its salts and esters, ethoxyfen, its salts and esters, fluoronitrofen, furyloxyfen, halosafen, chlomethoxyfen, fluoroglycofen, its salts and esters, lactofen, its salts and esters, oxyfluorfen, and fomesafen, its salts and esters); thiadiazoles (such as fluthiacet-methyl and thidiazimin); pyrimidinediones or phenyluracils (such as benzfendizone, butafenacil, ethyl [3-2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS Registry Number 353292-31-6 and referred to herein as S-3100), flupropacil, saflufenacil, and tiafenacil); phenylpyrazoles (such as fluazolate, pyraflufen and pyraflufen-ethyl); oxadiazoles (such as oxadiargyl and oxadiazon); triazolinones (such as azafenidin, bencarbazone, carfentrazone, its salts and esters, and sulfentrazone); oxazolidinediones (such as pentoxazone); N-phenylphthalimides (such as cinidon-ethyl, flumiclorac, flumiclorac-pentyl, and flumioxazin); benzoxazinone derivatives (such as 1,5-dimethyl-6-thioxo-3-(2,2,7-trifluoro-3,4-dihydro-3-oxo-4-prop-2-ynyl-2H-1,4-benzoxazin-6-yl)-1,3,5-triazinane-2,4-dione); flufenpyr and flufenpyr-ethyl; pyraclonil; and profluazol. Protoporphyrinogen oxidases and cells, seeds, plants, and plant parts provided by the invention exhibit herbicide tolerance to one or more PPO herbicide(s).

Herbicides may be applied to a plant growth area comprising the plants and seeds provided by the invention as a method for controlling weeds. Plants and seeds provided by the invention comprise an herbicide tolerance trait and as such are tolerant to the application of one or more PPO herbicides. The herbicide application may be the recommended commercial rate (1×) or any fraction or multiple thereof, such as twice the recommended commercial rate (2×). Herbicide rates may be expressed as acid equivalent per pound per acre (lb ae/acre) or acid equivalent per gram per hectare (g ae/ha) or as pounds active ingredient per acre (lb ai/acre) or grams active ingredient per hectare (g ai/ha), depending on the herbicide and the formulation. The herbicide application comprises at least one PPO herbicide. The plant growth area may or may not comprise weed plants at the time of herbicide application. A herbicidally effective dose of PPO herbicide(s) for use in an area for controlling weeds may consist of a range from about 0.1× to about 30× label rate(s) over a growing season. The 1× label rate for some exemplary PPO herbicides is provided in Table 2. One (1) acre is equivalent to 2.47105 hectares and one (1) pound is equivalent to 453.592 grams. Herbicide rates can be converted between English and metric as: (lb ai/ac) multiplied by 1.12=(kg ai/ha) and (kg ai/ha) multiplied by 0.89= (lb ai/ac).

TABLE 2

Exemplary PPO Herbicides

| PPO Herbicide | Chemical Family | 1X Rate |
| --- | --- | --- |
| acifluorfen | Diphenylethers | 420 g ai/ha |
| fomesafen | Diphenylethers | 420 g ai/ha |
| lactofen | Diphenylethers | 7-220 g ai/ha |
| fluoroglycofen-ethyl | Diphenylethers | 15-40 g ai/ha |
| oxyfluorfen | Diphenylethers | 0.28-2.24 kg ai/ha |
| flumioxazin | N-phenylphthalimide | 70 g ai/ha |
| azafenidin | Triazolinone | 240 g ai/ha |
| carfentrazone-ethyl | Triazolinone | 4-36 g ai/ha |
| sulfentrazone | Triazolinone | 0.1-0.42 kg ai/ha |
| fluthiacet-methyl | Thiadiazole | 3-15 g ai/ha |
| oxadiargyl | Oxadiazole | 50-150 g ai/ha |
| oxadiazon | Oxadiazole | 2.24-4.48 kg ai/ha |
| pyraflufen-ethyl | Phenylpyrazole | 6-12 g ai/ha |
| saflufenacil | Pyrimidine dione | 25-50 g/ha |
| S-3100 | Pyrimidine dione | 5-80 g/ha |

Herbicide applications may be sequentially or tank mixed with one, two, or a combination of several PPO herbicides or any other compatible herbicide. Multiple applications of one herbicide or of two or more herbicides, in combination or alone, may be used over a growing season to areas comprising transgenic plants of the invention for the control of a broad spectrum of dicot weeds, monocot weeds, or both, for example, two applications (such as a pre-planting application and a post-emergence application or a pre-emergence application and a post-emergence application) or three applications (such as a pre-planting application, a pre-emergence application, and a post-emergence application or a pre-emergence application and two post-emergence applications).

As used herein, "tolerance" or "herbicide tolerance" means a plant, seed, or cell's ability to resist the toxic effects of an herbicide when applied. Herbicide tolerant crops can continue to grow and are unaffected or minimally affected by the presence of the applied chemical. As used herein, an "herbicide tolerance trait" is a transgenic trait imparting improved herbicide tolerance to a plant as compared to the wild-type plant. Contemplated plants which might be produced with an herbicide tolerance trait of the present invention could include, for instance, any plant including crop plants such as soybean (e.g. *Glycine max*), corn (maize), cotton (*Gossypium* sp.), and canola, among others.

The transgenic plants, progeny, seeds, plant cells, and plant parts of the invention may also contain one or more additional traits. Additional traits may be introduced by crossing a plant containing a transgene comprising the recombinant DNA molecules provided by the invention with another plant containing one or more additional trait(s). As used herein, "crossing" means breeding two individual plants to produce a progeny plant. Two plants may thus be crossed to produce progeny that contain the desirable traits from each parent. As used herein "progeny" means the offspring of any generation of a parent plant, and transgenic progeny comprise a DNA construct provided by the invention and inherited from at least one parent plant. Additional trait(s) also may be introduced by co-transforming a DNA construct for that additional transgenic trait(s) with a DNA construct comprising the recombinant DNA molecules provided by the invention (for example, with all the DNA constructs present as part of the same vector used for plant transformation) or by inserting the additional trait(s) into a transgenic plant comprising a DNA construct provided by the invention or vice versa (for example, by using any of the methods of plant transformation or genome editing on a transgenic plant or plant cell). Such additional traits include, but are not limited to, increased insect resistance, increased water use efficiency, increased yield performance, increased drought resistance, increased seed quality, improved nutritional quality, hybrid seed production, and herbicide tolerance, in which the trait is measured with respect to a wild-type plant. Exemplary additional herbicide tolerance traits may include transgenic or non-transgenic tolerance to one or more herbicides such as ACCase inhibitors (for example aryloxyphenoxy propionates and cyclohexanediones), ALS inhibitors (for example sulfonylureas, imidazolinones, triazoloyrimidines, and triazolinones) EPSPS inhibitors (for example glyphosate), synthetic auxins (for example phenoxys, benzoic acids, carboxylic acids, semicarbazones), photosynthesis inhibitors (for example triazines, triazinones, nitriles, benzothiadiazoles, and ureas), glutamine synthesis inhibitors (for example glufosinate), HPPD inhibitors (for example isoxazoles, pyrazolones, and triketones), PPO inhibitors (for example diphenylethers, N-phenylphthalimide, aryl triazinones, and pyrimidinediones), and long-chain fatty acid inhibitors (for example chloroacetamindes, oxyacetamides, and pyrazoles), among others. Exemplary insect resistance traits may include resistance to one or more insect members within one or more of the orders of Lepidoptera, Coleoptera, Hemiptera, and Homoptera, among others. Such additional traits are well known to one of skill in the art; for example, and a list of such transgenic traits is provided by the United States Department of Agriculture's (USDA) Animal and Plant Health Inspection Service (APHIS).

A cell transformed with a polynucleotide of the present invention, such as an expression construct, may be selected for the presence of the polynucleotide or its encoded enzymatic activity before or after regenerating such a cell into a transgenic plant. Transgenic plants comprising such a polynucleotide may thus be selected for instance by identifying a transgenic plant that comprises the polynucleotide or the encoded enzymatic activity, and/or displays an altered trait relative to an otherwise isogenic control plant. Such a trait may be, for example, tolerance to a PPO herbicide.

Transgenic plants and progeny that contain a transgenic trait provided by the invention may be used with any breeding methods that are known in the art. In plant lines comprising two or more transgenic traits, the transgenic traits may be independently segregating, linked, or a combination of both in plant lines comprising three or more transgenic traits. Back-crossing to a parental plant and out-crossing with a non-transgenic plant are also contemplated, as is vegetative propagation. Descriptions of breeding methods that are used for different traits and crops are well known to those of skill in the art. To confirm the presence of the transgene(s) in a particular plant or seed, a variety of assays may be performed. Such assays include, for example, molecular biology assays, such as Southern and northern blotting, PCR, and DNA sequencing; biochemical assays, such as detecting the presence of a protein product, for example, by immunological means (ELISAs and western blots) or by enzymatic function; plant part assays, such as leaf or root assays; and also, by analyzing the phenotype of the whole plant.

Introgression of a transgenic trait into a plant genotype is achieved as the result of the process of backcross conversion. A plant genotype into which a transgenic trait has been introgressed may be referred to as a backcross converted genotype, line, inbred, or hybrid. Similarly a plant genotype lacking the desired transgenic trait may be referred to as an unconverted genotype, line, inbred, or hybrid.

Having described the invention in detail, it will be apparent that modifications, variations, and equivalent embodiments are possible without departing the scope of the invention defined in the appended claims. Furthermore, it should be appreciated that the examples in the present disclosure are provided as non-limiting examples.

EXAMPLES

The following examples are included to demonstrate embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit, and scope of the invention. More specifically, it will be apparent that certain agents which are both chemically and physiologically related may be substituted for the agents described herein with the same or similar result achieved. All such similar substitutes and modifications apparent to those skilled in the art are deemed to be within the spirit, scope, and concept of the invention as defined by the appended claims.

Example 1: Microbial Protoporphyrinogen Oxidase Discovery

Novel protoporphyrinogen oxidases were identified from microbial sequence databases using bioinformatic methods and a novel protoporphyrinogen oxidase bacterial screening system. The sequence of E. coli HemG (SEQ ID NO:4) was use as a starting sequence for bioinformatic analysis of microbial sequence databases. The bioinformatic analysis identified thirty-three novel putative protoporphyrinogen oxidases of the HemG PPO family from diverse bacterial sources. The sequences encoding these putative HemG PPO enzymes were compared using phylogenetic tree mapping and found to be relatively diverse. Ten were selected for further analysis from this group of thirty-three due to their representation of individual unique clustered members on the phylogenetic tree.

The coding sequences for the ten selected HemG PPO enzymes were optimized for E. coli expression to eliminate any rare codons found in the wild-type DNA sequence. The E. coli optimized coding sequences for the ten HemG PPO enzymes were then cloned into bacterial expression vectors. An herbicide-sensitive PPO enzyme found naturally in waterhemp (Amaranthus tuberculatus) was cloned into a bacterial expression vector for use as a control for both PPO function and herbicide-sensitivity (referred to as "WH" and provided as SEQ ID NO:21; NCBI GenBank Accession No. ABD52326; Patzoldt, et al. "A codon deletion confers resistance to herbicides inhibiting protoporphyrinogen oxidase" Proceedings of the National Academy of Science USA. 103(33):12329-12334 (2006)). The waterhemp PPO enzyme is not a HemG family member. The HemG PPO enzyme found naturally in E. coli was cloned into a bacterial expression vector for use as a control for both PPO activity and to assay it for herbicide-sensitivity (referred to as H_N10 and provided as SEQ ID NO:4).

A protoporphyrinogen oxidase bacterial screening system was created to test recombinant proteins for protoporphyrinogen oxidase activity and thus confirm that they are functional PPO enzymes. This screening system used a functional rescue assay in an E. coli strain that contained a gene knockout for the E. coli PPO enzyme (SEQ ID NO:4). The hemG knockout E. coli strain which was utilized showed very minimal growth on heme-free bacterial medium (such as LB medium), but growth was recovered when the bacterial medium was supplemented with free heme or when an active recombinant protoporphyrinogen oxidase was expressed in the E. coli. The hemG knockout E. coli strain could thus be used with recombinant protein expression to quickly and easily assay proteins for protoporphyrinogen oxidase activity.

The hemG knockout E. coli strain was transformed with bacterial expression vectors containing the gene encoding the ten putative HemG PPO enzymes, the E. coli HemG PPO enzyme, and the waterhemp PPO enzyme. The bacteria were then streaked onto LB medium plates, which is a heme-free bacterial medium. Expression of a recombinant PPO enzyme rescued the growth of E. coli, resulting in growth on the LB plates. Growth of the transformed hemG knockout E. coli strain on LB plates indicated that a protein sequence functioned as a protoporphyrinogen oxidase. Ten HemG PPO enzymes (SEQ ID NOs:1-10), and the waterhemp PPO enzyme (SEQ ID NO:21) were able to restore growth of the transformed hemG knockout E. coli strain in this assay, thus confirming their PPO activity. An alignment of the protein sequences of PPO enzymes, with consensus positions, is provided as FIG. 1. Using this assay, a large number of novel or engineered proteins can be screened to confirm and measure protoporphyrinogen oxidase activity.

Example 2: Protoporphyrinogen Oxidase Inhibitor Insensitivity

Novel protoporphyrinogen oxidases that are tolerant to PPO herbicides were identified using an herbicide bacterial screening system. This screening system used a growth assay of the hemG knockout E. coli strain in LB liquid medium with a PPO herbicide to identify protoporphyrinogen oxidases that were not sensitive to the PPO herbicide.

The hemG knockout E. coli strain was transformed with a bacterial expression vector containing the confirmed protoporphyrinogen oxidase activity and cultured in LB liquid medium. Purified crystalline form of one of five different PPO herbicides (acifluorfen (1 mM), flumioxazin (0.5 mM), lactofen (0.5 mM), fomesafen (1 mM), and S-3100 (100 uM), representing three different PPO chemistry subclasses, was added to the medium. Recombinant proteins were expressed and the E. coli growth rates were measured. Growth curves (OD600) were measured for the different variants in the presence and absence of the PPO herbicides at selected time-points from time zero to twenty-four hours. The growth of a transformed hemG knockout E. coli strain in LB medium in the presence of a PPO herbicide indicated that the gene used to transform the E. coli encoded an herbicide-insensitive protoporphyrinogen oxidase (iPPO).

Novel protoporphyrinogen oxidases were used with this assay to test for insensitivity to PPO herbicides. The ten protoporphyrinogen oxidases provided as SEQ ID NO: 1 through SEQ ID NO:10 were all found to confer normal growth rates on the hemG knockout E. coli strain in LB medium in the presence of a PPO herbicide, indicating that these proteins are herbicide-insensitive protoporphyrinogen oxidases (iPPO) (FIG. 2). The hemG knockout E. coli strain expressing the waterhemp PPO (SEQ ID NO:21) was sensitive to all five PPO herbicides, confirming that the assay was able to distinguish between sensitive and insensitive protoporphyrinogen oxidases for each of the herbicides. Using this assay, a large number of novel or engineered proteins can be screened to confirm protoporphyrinogen oxidase activity in the presence of PPO herbicide(s).

Example 3: Protoporphyrinogen Oxidase (PPO) Enzyme Assay

Protoporphyrinogen oxidases were enzymatically characterized to measure each PPO enzyme's substrate binding affinity ($K_m$) and sensitivity to the PPO herbicide (IC50). Wild-type plant PPO enzymes from waterhemp, soybean, and maize were used for comparison to the microbial HemG protoporphyrinogen oxidases (provided as SEQ ID NO: 1 through SEQ ID NO:10).

Etioplasts and chloroplasts were prepared from etiolated cotyledons (soybean, *Glycine max*), etiolated leaves/coleoptiles (maize, *Zea mays*) and unfolded apical leaves (waterhemp, *Amaranthus tuberculata*) generally by the procedure described by Grossmann et al., ("The Herbicide Saflufenacil (Kixor™) is a New Inhibitor of Protoporphyrinogen IX Oxidase Activity" Weed *Science,* 58(1):1-9 (2010)). Soybean (A3555) and maize (LH244) seeds were placed between two sheets of moist germination paper (Anchor Paper Company, Saint Paul, Minn., USA) in a beaker of water in continuous darkness for eight to ten days. Waterhemp plants were grown for 30 days in the greenhouse. Tissue was collected, placed between moist sheets of paper towels until ground to fine powder with a mortar and pestle in liquid nitrogen. Homogenization buffer (50 mM Tris-HCl, pH 7.4, 500 mM sucrose, 1 mM EDTA, 1 mM magnesium chloride, and 2 g/liter bovine serum albumin) was added to the frozen powder at 4:1 (ml homogenization buffer to g fresh weight tissue), mixed vigorously and filtered through four layers of pre-moistened Miracloth™ (Merck-Millipore, Darmstadt, Germany). The filtrate was centrifuged at 9299 g for five minutes. The pellet was re-suspended in homogenization buffer and centrifuged at 150 g for two minutes. The supernatant solution was centrifuged at 4000 g for fifteen minutes. All centrifugation steps were carried out a 4° C. The pellet (intact plastid fraction) was re-suspended in 50 mM Tris-HCl (pH 7.4), 2 mM EDTA and 20% (v/v) glycerin and stored in aliquots at −80° C. Total protein in plastid preparations was measured by the Bradford method (MM Bradford, "A rapid and sensitive method for the quantitation of microgram quantities of protein utility the principle of protein-dye binding" Analytical Biochemistry, 72:248-254 (1976)) with bovine serum albumin as the standard.

Selected PPO enzymes were expressed in the *E. coli* hemG knockout cell line. Bacterial cells from an overnight culture were used to inoculate 20 ml of fresh media. These cultures were allowed to grow for approximately 48 hrs at 20° C. to a dense culture. Bacterial cells were collected by centrifugation and the cell pellets stored at −80° C. until enzyme assays were performed. Frozen bacterial pellets were re-suspended in extraction buffer (50 mM Tris-HCl, pH 7.6, 1 mM EDTA & 1 mM $MgCl_2$) and sonicated (Sonics VibraCell™, Newtown, Conn. USA) for three cycles of 30 seconds in an ice bath with a one-minute rest period between cycles. Broken cells were centrifuged at 200 g for 2 minutes at 4° C. and the supernatant solution was used for PPO enzyme assays after dilution with extraction buffer. Total protein was measured by the method of Bradford (1976) with bovine serum albumin as the standard.

Protoporphryinogen IX (protogen) was synthesized by reduction of commercially-available protoporphyrin with sodium mercury amalgam as described by J M Jacobs and N J Jacobs ("Measurement of Protoporphyrinogen Oxidase Activity" in *Current Protocols in Toxicology* (1999) 8.5.1-8.5.13, John Wiley & Sons, Inc.). Protoporphyrin (Proto) was added to 0.01N potassium hydroxide in 20% ethanol and stirred in the dark until dissolved (about 40 minutes). A volume of 0.8 ml of was placed in a 2-ml polypropylene vial with a screw-top cap containing an O-ring, and about 1 g (a spatula tipful, oil drained off) of sodium mercury amalgam (Product Number 451908, Sigma-Aldrich, St. Louis, Mo., stored under oil) was added. The tube was immediately capped and mixed vigorously with a vortex mixer and vented about every 30 seconds by loosening the cap until the solution was no longer fluorescing red under a UV light (about five minutes). The reaction vial was flushed with argon and centrifuged briefly to pellet the remaining sodium amalgam. The supernatant solution was immediately diluted 1:1 (v/v) with a solution of 0.1M DTT and 0.5M Tris-HCl, pH 7.5 and the vial flushed with argon. The resulting solution was split into smaller aliquots into 0.5 ml polypropylene capped tubes which were flushed with argon immediately after the aliquot was added. Capped tubes were covered with aluminum foil and stored at −80° C. For the enzyme assay, the protogen aliquots were thawed, stored covered on ice, and used on the same day. The concentration of protogen in the preparation was calculated by subtracting the Proto concentration, as measured by fluorescence HPLC (method described by Matsumoto et al, "Porphyrin Intermediate Involved in Herbicidal Action of delta-Aminolevulinic Acid on Duckweed (*Lemna paucicostata* Hegelm.)" *Pesticide Biochem. and Phys.* 48:214-221 (1994)), in the final protogen solution (typically about 1% of starting material) from the Proto concentration in the starting material and assuming no significant impurities in either sample. Protogen prepared and stored under these conditions was stable for at least six months.

PPO activity in plant plastid extract and bacterial extract preparations was measured generally as described by Grossmann. et al. (2010). Ten microliters of either plastid extract (40 μg total protein) or bacterial extract (16 to 35 μg total protein for the different bacterial extracts) was added to assay buffer (100 mM Tris-HCl, pH 7.4, 5 mM DTT, 1 mM EDTA and 0.085% (v/v) Tween 80). S-3100 (also known as "SYN-523"; e.g. U.S. Patent Publication US20100062941 A1) was added as a two-microliter volume from a 100× stock solution prepared in acetone. Analytical-grade S-3100 was provided by Sumitomo Chemical Company. All assays were run in a final concentration of 1% (v/v) acetone. The extracts (plastid or bacterial), buffer, and S-3100 were incubated at 30° C. (plant extracts) or 37° C. (bacterial extracts) for five minutes before addition of two microliters of protogen to initiate the assay. All assays were done in a 96-well black polystyrene microtiter plate (Costar® 3925, Corning, Inc., Corning, N.Y.) at a final volume of 200 microliters. After protogen addition (3 μM for $IC_{50}$ measurements; variable for $K_m$ measurements) to all wells, the plate was incubated at 30° C. (plant extracts) or 37° C. (bacterial extracts) before initiating data collection. Fluorescence over time was measured at 30° C. (plant extracts) or 37° C. (bacterial extracts) with excitation and emission wavelengths of 405 mm and 630 mm, respectively, in a SpectraMax® M5 Multi-Mode Microplate Reader (Molecular Devices, Sunnyvale, Calif.). An assay blank was run by adding heat-inactivated (five minutes at 100° C.) extract to the assay mixture.

Substrate (protoporphyrinogen) binding affinity of protoporphyrinogen oxidases was measured as the $K_m$. The apparent $K_m$ values for each PPO evaluated were calculated using rectangular hyperbola curve-fitting using the SoftPro® kinetics software package (Molecular Devices, Sunnyvale, Calif.). Enzyme activity sensitivity to the PPO herbicide S-3100 was measured as the concentration giving 50% inhibition of control activity ($IC_{50}$). The S-3100 $IC_{50}$ values for each PPO evaluated were determined graphically from the semi logarithmic plot of S-3100 concentration versus PPO activity.

The $K_m$ for the PPO enzymes from three plant sources (waterhemp, soybean, or maize) and the microbial HemG PPO enzymes (SEQ ID NO: 1 through SEQ ID NO:10) were found to be similar, ranging from 0.3 uM to 2.0 uM. The three plant PPO enzymes tested were sensitive to S-3100 with $IC_{50}$ values of 0.009, 0.004, and 0.003 uM, respectively. In contrast, the PPO enzymes from a bacterial source (SEQ ID NO: 1 through SEQ ID NO:10) were insensitive to S-3100 with $IC_{50}$ values greater than 100 uM. Data are provided in Table 3.

TABLE 3

PPO enzymatic activity of enzymes purified from plant or microbial sources

| Source | $K_m$ (uM) | S-3100 $IC_{50}$ (uM) |
|---|---|---|
| Waterhemp | 0.7 | 0.009 |
| Soybean | 1.8 | 0.004 |
| Maize | 2.0 | 0.003 |
| H_N10 (SEQ ID NO: 4) | 0.7 | >100 |
| H_N20 (SEQ ID NO: 2) | 0.8 | >100 |
| H_N30 (SEQ ID NO: 5) | 1.0 | >100 |
| H_N40 (SEQ ID NO: 6) | 1.4 | >100 |
| H_N50 (SEQ ID NO: 7) | 1.0 | >100 |
| H_N60 (SEQ ID NO: 3) | 1.1 | >100 |
| H_N70 (SEQ ID NO: 8) | 1.4 | >100 |
| H_N90 (SEQ ID NO: 1) | 1.2 | >100 |

TABLE 3-continued

PPO enzymatic activity of enzymes purified from plant or microbial sources

| Source | $K_m$ (uM) | S-3100 $IC_{50}$ (uM) |
|---|---|---|
| H_N100 (SEQ ID NO: 9) | 0.6 | >100 |
| H_N110 (SEQ ID NO: 10) | 0.3 | >100 |

Example 4: Enzymatic Optimization of Protoporphyrinogen Oxidases

Protein optimization is used to improve or alter the enzymatic properties of novel protoporphyrinogen oxidases. One or more methods of protein engineering are used to optimize the enzymes. Non-limiting examples of protein engineering approaches include Alanine-Scanning Mutations; Homology-Scanning Mutations; Pro/Gly Scanning Mutations; Region Swaps or Mutations; and combinations of these various techniques (see, M Lehmann and M Wyss, Current Opinion in Biotechnology 12(4):371-375 (2001); B Van den Burg and VGH Eijsink, Current Opinion in Biotechnology 13(4):333-337 (2002); and Weiss et al., Proceedings of the National Academy of Sciences USA 97(16):8950-8954 (2000)). DNA sequences encoding engineered protoporphyrinogen oxidases are synthesized and cloned into the bacterial expression vector. The vector is used to transformed the hemG knockout E. coli strain for the initial high-throughput bacterial rescue screen as described in Example 1. The engineered protoporphyrinogen oxidases that rescue the hemG knockout E. coli strain are screened for sensitivity to one or more PPO herbicide(s) using the bacterial growth assay as described in Example 2. Alternatively, the transformed hemG knockout E. coli strain is plated on medium with and without a PPO herbicide. The engineered variants that exhibit tolerance to PPO herbicides are expressed in a bacterial expression system and a detailed biochemical characterization is done using the purified protein with the continuous fluorimetric assay as described in Example 3. The engineered variants that are insensitive to PPO herbicides are selected for cloning into plant transformation vectors, plant transformation, and in planta testing.

Example 5: Expression and Testing of HemG PPO Enzymes in Maize

The microbial HemG PPO enzymes were expressed in transgenic maize plants, and the transgenic plants were analyzed for PPO herbicide tolerance. Plant transformation vectors were constructed comprising a recombinant DNA molecule encoding one of the microbial HemG PPO enzymes provided as SEQ ID NO: 1-20. The DNA sequence encoding a PPO enzyme can include at the 5' end a codon for a methionine, commonly known as a start codon, or this codon can be eliminated to facilitate operable linkage of a transit peptide sequence to the 5' end of the coding sequence. Examples of PPO enzyme protein sequences containing a methionine at the amino-terminus are provided as SEQ ID NO:1-10. Examples of PPO enzyme protein sequences without a methionine at the amino-terminus are provided as SEQ ID NO:11-20. For plant transformation, the nucleotide sequences encoding the putative PPO enzymes were codon optimized for either dicot or monocot expression. Table 4 provides the SEQ ID NO corresponding to the protein and nucleotide sequences of the microbial HemG PPO enzymes in the transformation vectors.

TABLE 4

SEQ ID NO corresponding to PPO variants

| PPO | Protein | Bacterial DNA | Dicot codon optimized | Monocot codon optimized |
|---|---|---|---|---|
| H_N10 | 4, 13 | 25 | 35, 44 | 57 |
| H_N20 | 2, 12 | 23 | 33, 43, 52 | 55 |
| H_N30 | 5, 14 | 26 | 36, 45 | 58 |
| H_N40 | 6, 15 | 27 | 37, 46 | 59 |
| H_N50 | 7, 16 | 28 | 38, 47 | 60 |
| H_N60 | 3 | 24 | 34 | 56 |
| H_N70 | 8 | 29 | 39 | 61 |
| H_N90 | 1, 11, 18, 19 | 22 | 32, 42, 49, 50, 51 | 54 |
| H_N100 | 9, 17, 20 | 30 | 40, 48, 53 | 62 |
| H_N110 | 10 | 31 | 41 | 63 |
| Waterhemp PPO | 21 | n/a | n/a | n/a |

Four plant transformation vectors were created for expressing the HemG PPO H_N10 (SEQ ID NO:4) using two different combinations of promoter plus leader plus intron with two different targeting peptide (TP) sequences and two different 3'UTR sequences. The plant transformation constructs were annotated construct 1, 6, 11, and 16. For maize in planta testing, immature maize (LH244) embryos were transformed with using Agrobacterium tumefaciens and standard methods known in the art.

Transgenic maize plants were produced using the plant transformation constructs 6 and 16 containing the gene encoding the HemG PPO H_N10 (SEQ ID NO:4). Leaf samples were collected from R0 plants and screened by PCR to determine the number of copies of the transgene inserted into the plant genome. The plants containing a single copy (single copy) were selfed and outcrossed to generate R1 and F1 seed for future testing, respectively. Plants containing multiple copies (multi-copy) were sprayed as follows: (1) 5 g/ha S-3100 at approximately the V5 growth stage followed by 10 g/ha S-3100 at approximately the V7 growth stage, for a total application of 15 g/ha S-3100 or (2) 10 g/ha S-3100 at approximately the V5 growth stage. The average percentage of injury, on a scale of 0-100 with zero being no injury and 100 being complete crop death, was assessed 7 days after the final treatment for each batch. Sprayed non-transgenic LH244 maize was used as a control and showed an average of 43.3% injury when treated with a total of 15 g/ha S-3100 (Treatment 1) and an average injury of 26.7% when treated with a total of 10 g/ha S-3100 (Treatment 2). Transgenic maize plants expressing HemG H_N10 (SEQ ID NO:4) outperformed the control plants with an average of 28.9% injury when treated with a total of 15 g/ha S-3100 (Treatment 1) and an average injury of 24.2% when treated with a total of 10 g/ha S-3100 (Treatment 2). Data are provided in Table 5.

TABLE 5

Transgenic Maize Herbicide Tolerance I

| Treatment | Protein | Construct | Plants Tested | Average Injury |
|---|---|---|---|---|
| 1 | n/a | nontransgenic | 12 | 43.3 |
| 1 | H_N10 | 6 | 18 | 28.9 |
| 2 | n/a | nontransgenic | 6 | 26.7 |
| 2 | H_N10 | 16 | 12 | 24.2 |

Transgenic maize plants were produced using the plant transformation constructs 6, 20, 21, 22, and 23 containing the gene encoding the HemG PPO enzymes H_N90 (SEQ ID NO:1), H_N10 (SEQ ID NO:4), H_N60 (SEQ ID NO:3), H_N110 (SEQ ID NO:10), and H_N40 (SQ ID NO:6), respectively. These five constructs had the same promoter plus leader plus intron combination, with two different targeting peptide (TP) sequences, and the same 3'UTR sequence. Leaf samples were taken from the R0 plants and analyzed by PCR to determine the transgene copy number. Single copy plants for up to 12 unique events per construct were transplanted to pots, selfed and outcrossed to generate R1 and F1 seed, respectively, for future testing. Multi-copy plants and extra single copy plants were sprayed with 40 grams/ha S-3100 at approximately the V5 growth stage and injury ratings were taken 7 days after treatment. The average percent (%) injury for all plants expressing each PPO enzyme and the number of plants that were deemed highly tolerant (less than 10% injury) was noted, where each plant is a unique single or multi-copy transformant. Transgenic maize plants expressing H_N10 (SEQ ID NO:4) had an overall average injury of 39.5% and produced 31 highly tolerant plants out of 139 plants tested. Transgenic maize plants expressing H_N60 (SEQ ID NO:3) had an overall average injury of 55.8% and produced 19 highly tolerant plants out of the 86 plants tested. Transgenic maize plants expressing H_N90 (SEQ ID NO:1) had the lowest overall average injury at 31.4% and produced 44 highly tolerant plants out of the 99 plants tested. Transgenic maize plants expressing H_N40 (SEQ ID NO:6) had an overall average injury at 47.0% and produced the highest proportion of highly tolerant plants with 53 highly tolerant plants out of the 98 plants tested. Transgenic maize plants expressing H_N110 (SEQ ID NO:10) had an average injury of 43.0% but did not produce any highly tolerant plants. Data are provided in Table 6.

TABLE 6

Transgenic Maize Herbicide Tolerance II

| Construct | Protein | SEQ ID NO | Plants Tested | Average Injury | Highly Tolerant |
|---|---|---|---|---|---|
| 6 | H_N10 | 4 | 139 | 39.5% | 31 |
| 20 | H_N60 | 3 | 86 | 55.8% | 19 |
| 21 | H_N90 | 1 | 99 | 31.4% | 44 |
| 22 | H_N110 | 10 | 94 | 43.0% | 0 |
| 23 | H_N40 | 6 | 98 | 47.0% | 53 |

The R0 transgenic maize data demonstrated that the five microbial HemG PPO enzymes H_N90 (SEQ ID NO:1), H_N10 (SEQ ID NO:4), H_N60 (SEQ ID NO:3), H_N40 (SEQ ID NO:6), and H_N110 (SQ ID NO:10) produced reduced injury rates when expressed in transgenic plants and thus conferred crop tolerance to a PPO herbicide.

Transgenic F1 plants produced from outcrossing the single copy R0 plants expressing H_N10 (SEQ ID NO:4) in one of two construct configurations were tested in the greenhouse for herbicide tolerance. The plants were treated with 40 grams/ha S-3100 at the V3 growth stage and injury ratings were taken seven days after treatment. Transgenic maize plants expressing H_N10 (SEQ ID NO:4) in the construct 6 configuration resulted in 13 out of 18 events producing highly tolerant plants (10% or less injury) but the construct 16 configuration resulted in no events producing highly tolerant plants.

Transgenic F1 plants produced from outcrossing the single copy R0 plants expressing H_N10 (SEQ ID NO:4) in one of two construct configurations (constructs 6 and 16) were tested in the field for herbicide tolerance. This F1 population was segregating (50% hemizygous and 50% null) and selection for transgenic plants was not conducted prior to injury ratings. The overall average injury ratings for such a population are expected to be higher than a homogenous transgenic population since it is difficult to discern non-transgenic plants from transgenic plants. The trials were conducted at two locations with two replicates and 3 treatments per construct. Non-transgenic maize plants were used as a negative control. The herbicide application treatments were as follows: Treatment 1 was 0.036 lb ai/acre S-3100 applied at V2 followed by (fb) V4 fb V8; Treatment 2: was 0.072 lb ai/acre S-3100 applied at V2 fb V4 fb V8; Treatment 3: was 0.144 lb ai/acre S-3100 applied at V2 fb V4 fb V8. Crop Injury Percent ratings were assessed at the V2 growth stage (CIPV2) and at the V4 growth stage (CIPV4) at 5 to 7 days after treatment (the error V2 and error V4 are half of the least significant difference (LSD)). The crop injury ratings were combined for both locations. All non-transgenic plants and plants with events generated using construct 16 showed between 94.6-99.5% injury following both the V2 and V4 herbicide application for each of the three treatments. Plants with events generated using construct 6 showed only 30% to 50% injury following the V2 herbicide application and no injury following the V4 herbicide application. Data are provided in Table 7.

TABLE 7

Efficacy field trial of F1 maize containing H_N10 (SEQ ID NO: 4)

| Treatment | Construct | CIPV2 | CIPV4 | Error V2 | Error V4 |
|---|---|---|---|---|---|
| Trt 1 | wildtype | 94.6 | 99 | 8.6 | 1.2 |
|  | 6 | 37.5 | 0 | 8.6 | 1.2 |
|  | 16 | 96.3 | 98.5 | 8.6 | 1.2 |
| Trt 2 | wildtype | 99.5 | 99.5 | 5.4 | 0 |
|  | 6 | 37.5 | 0 | 5.4 | 0 |
|  | 16 | 99.5 | 99.5 | 5.4 | 0 |
| Trt 3 | wildtype | 99.5 | 99.5 | 0 | 0 |
|  | 6 | 50 | 0 | 0 | 0 |
|  | 16 | 99.5 | 99.5 | 0 | 0 |

The F1 transgenic maize greenhouse and field data demonstrated that the microbial HemG PPO enzyme H_N10 (SEQ ID NO:4) produced reduced injury rates when expressed in transgenic plants and thus conferred crop tolerance to a PPO herbicide.

Example 6: Expression and Testing of HemG PPO Enzymes in Soybean Plants

The microbial HemG PPO enzymes were expressed in transgenic soybean plants, and the transgenic plants were analyzed for PPO herbicide tolerance. Plant transformation vectors were constructed comprising a recombinant DNA molecule encoding one of the microbial HemG PPO enzymes provided as H_N10 (SEQ ID NO:4 and SEQ ID NO:13); H_N20 (SEQ ID NO:12); H_N30 (SEQ ID NO:14); H_N40 (SEQ ID NO:15); H_N50 (SEQ ID NO:16); H_N90 (SEQ ID NO:11, 18, 19); and H_N100 (SEQ ID NO:17, 20).

In soybean, excised embryos (A3555) were transformed with the transformation constructs 1 and 11 using *A. tumefaciens* and standard methods known in the art. Transformation constructs 1 and 11 had the same promoter plus leader plus intron combination, the same 3'UTR sequence, the same microbial HemG PPO H_N10 (SEQ ID NO:4), but differed in the targeting peptide (TP) sequences. Regenerated R0 transgenic plantlets were grown in the greenhouse.

Plants representing twenty single copy R0 soybean events produced from construct 11 and expressing the microbial PPO enzyme H_N10 (SEQ ID NO: 4) were sprayed with 210 g/ha flumioxazin (Valor®, Valent U.S.A. Corporation, Walnut Creek Calif.). The herbicide was sprayed at the V3 developmental stage with three fully developed trifoliate leaves and injury ratings were assessed 8 days after treatment. The percentage of plants that were deemed highly tolerant (15% or less injury) was noted. After application of 210 g/ha flumioxazin, the non-transgenic soybean control plants had an average injury rating of 30% and no highly tolerant plants. Soybean plants expressing the microbial PPO enzyme H_N10 (SEQ ID NO:4) had an average injury rating of 22%, and 9% of the plants tested were highly tolerant to the herbicide.

Plants representing ten multi-copy R0 soybean events produced from construct 11 and expressing the microbial PPO enzyme H_N10 (SEQ ID NO: 4) were sprayed with 5 g/ha S-3100. The herbicide was sprayed at the V3 developmental stage with three fully developed trifoliate leaves and injury ratings taken 8 days after treatment. The percentage of plants that were deemed highly tolerant (25% or less injury) was noted. After application of S-3100 (5 g/ha), the non-transgenic soybean control plants had an average injury rating of 60% and no highly tolerant plants. Soybean plants expressing the microbial PPO enzyme H_N10 (SEQ ID NO: 4) had an average injury rating of 47%, and 30% of the plants tested were highly tolerant to the herbicide.

Single-copy transgenic R1 soybean plants in the greenhouse were sprayed with one of three herbicide application rates: Treatment 1 was 5 grams ai/ha S-3100 applied at V4 followed by (fb) R1; Treatment 2 was 10 grams ai/ha S-3100 applied at V4 fb R1; Treatment 3 was 30 grams ai/ha S-3100 applied at V4 fb R1. Crop Injury Percent at V2 (CIPV2) ratings were assessed ten days after treatment. Non-transgenic plants had average injury ratings of 89% to 100% and were not available for rating at the R1 growth stage. The plants produced from construct 1 and expressing the microbial PPO enzyme H_N10 (SEQ ID NO: 4) had injury ratings ranging from 3% to 15.7%. Data are provided in Table 8.

TABLE 8

Green house S-3100 efficacy screen of R1 soybean

| Construct | Treatment | S-3100 Rate | % Injury V4 stage | % Injury R1 stage |
|---|---|---|---|---|
| 1 | 1 | 5 g/ha | 4.2 | 3 |
| 1 | 2 | 10 g/ha | 7.8 | 6.5 |
| 1 | 3 | 30 g/ha | 9.4 | 15.7 |
| Nontransgenic | 1 | 5 g/ha | 89 | |
| Nontransgenic | 2 | 10 g/ha | 98 | |
| Nontransgenic | 3 | 30 g/ha | 100 | |

A high-throughput plant transformation and screening method was used to evaluate large numbers of constructs in transgenic plants for herbicide tolerance in early transformation plantlet tissue. This allowed for faster and higher volume screening of construct configurations and PPO enzymes.

The genes encoding the seven microbial HemG PPO enzymes H_N10 (SEQ ID NO:13); H_N20 (SEQ ID NO:12); H_N30 (SEQ ID NO:14); H_N40 (SEQ ID NO:15); H_N50 (SEQ ID NO:16); H_N90 (SEQ ID NO:11, 18, 19); and H_N100 (SEQ ID NO:17, 20) were operably linked to thirty-seven different targeting peptides and cloned into a base plant transformation vector. This permitted the side-by-side comparison of seven different HemG PPO enzymes with thirty-seven different targeting peptides using the same promoter and 3'UTR elements for gene expression. These plant transformation constructs were used to transform soybean excised embryos (germplasm A3555) using *A. tumefaciens* and standard methods known in the art. Four hundred explants were inoculated for each construct resulting in twelve containers per construct. A sterile PPO herbicide solution was used for herbicide tolerance testing. The herbicide solution consisted of 0.3 g of S-3100 in crop oil concentrate (5.0 mL) and 495 mL of deionized water. This was filtered through a 0.45 micron Nalgene® Rapid-Flow™ Tissue Culture Filter Unit and Surfactant-Free Cellulose Acetate membrane filter unit (VWR, Radnor, Pa., USA). The resulting sterile solution was shaken before application.

At five weeks post-transformation, four of the twelve plant containers per construct were sprayed with two passes of the sterile PPO herbicide solution. The treated plantlets were then enclosed in the container and received at least 15 hours of light exposure post spray each day for four days. At the end of day four post application of S-3100, the treated plantlets were photographed and scored on a visual scale of green coloration (green coloration was representative of healthy photosynthetic plant tissue as compared to photobleached tissue) versus damage. The scoring values were 0 for poor tolerance, high damage, low green coloration; 1 for some tolerance, average damage, moderate green coloration; and 2 for good tolerance, low damage, high green coloration. The scoring for each construct is presented in Table 9, where n.d. indicates the analysis was not conducted. The results indicate that in this high-throughput screening a number constructs provided tolerance to the PPO herbicide.

TABLE 9

High-throughput soybean screening for herbicide tolerance: coloration score

| Targeting Peptide | H_10 | H_N20 | H_N30 | H_N40 | H_N50 | H_N90 | H_N100 |
|---|---|---|---|---|---|---|---|
| TP1 | n.d. | 0 | 2 | 2 | 1 | 2 | 2 |
| TP2 | n.d. | 0 | 0 | 1 | 1 | 2 | 1 |
| TP3 | 1 | 1 | n.d. | 1 | 1 | 2 | 1 |
| TP4 | n.d. | 1 | n.d. | 2 | 1 | 1 | n.d. |
| TP5 | n.d. | n.d. | n.d. | n.d. | 0 | 1 | n.d. |
| TP6 | 0 | 1 | 0 | n.d. | 2 | 2 | 2 |
| TP7 | n.d. | 2 | 1 | 2 | 1 | 2 | 2 |
| TP8 | 0 | 1 | 1 | 2 | 1 | 0 | 0 |

TABLE 9-continued

High-throughput soybean screening for herbicide tolerance: coloration score

| Targeting Peptide | H_10 | H_N20 | H_N30 | H_N40 | H_N50 | H_N90 | H_N100 |
|---|---|---|---|---|---|---|---|
| TP9 | 1 | 1 | 1 | 0 | 1 | 1 | 0 |
| TP10 | n.d. | n.d. | 0 | n.d. | 1 | 2 | 1 |
| TP11 | n.d. | 1 | 1 | 1 | 0 | 2 | 0 |
| TP12 | 1 | 2 | 1 | 1 | 1 | 2 | 2 |
| TP13 | 1 | 2 | 1 | 1 | 1 | 2 | 0 |
| TP14 | 0 | 0 | n.d. | 2 | 1 | 2 | 1 |
| TP15 | n.d. | 1 | 1 | 2 | 2 | 2 | 2 |
| TP16 | 1 | 1 | n.d. | n.d. | 0 | 1 | 1 |
| TP17 | n.d. | 2 | 1 | 1 | 1 | 2 | 1 |
| TP18 | 1 | 1 | 0 | 1 | 1 | 2 | 1 |
| TP19 | 0 | 1 | 0 | 1 | 0 | 1 | 1 |
| TP20 | 0 | 2 | n.d. | n.d. | n.d. | 2 | 2 |
| TP21 | 0 | 0 | n.d. | 2 | 1 | 1 | 0 |
| TP22 | 1 | 1 | n.d. | n.d. | 2 | 2 | 2 |
| TP23 | 1 | 1 | n.d. | 1 | 1 | 1 | 2 |
| TP24 | 0 | 1 | 1 | 0 | 1 | 1 | 0 |
| TP25 | n.d. | 1 | n.d. | 2 | 2 | 1 | 1 |
| TP26 | 0 | 1 | 0 | 1 | 1 | 0 | n.d. |
| TP27 | 1 | 1 | 0 | 1 | 1 | 1 | 1 |
| TP28 | n.d. | 1 | 0 | 1 | 1 | 2 | 1 |
| TP29 | n.d. | 1 | 1 | 1 | 1 | 1 | 1 |
| TP30 | n.d. | 1 | n.d. | 1 | 1 | 1 | 1 |
| TP31 | 1 | 1 | n.d. | 1 | 0 | 0 | 1 |
| TP32 | n.d. | 0 | n.d. | 1 | 1 | 0 | 2 |
| TP33 | 1 | 1 | 1 | 0 | 1 | 2 | 1 |
| TP34 | n.d. | n.d. | n.d. | n.d. | 0 | 2 | 0 |
| TP35 | n.d. | n.d. | n.d. | n.d. | n.d. | 1 | 1 |
| TP36 | 0 | n.d. | n.d. | n.d. | 0 | 2 | 1 |
| TP37 | n.d. | n.d. | n.d. | n.d. | 0 | n.d. | n.d. |

The plantlets in the non-sprayed containers corresponding to constructs having a score of 2 were transplanted at approximately 7 weeks post transformation and grown as R0 plants using standard methods known in the art. Plantlets corresponding to non-tolerant scores of 0 and 1 were also grown to serve as negative controls. The R0 plants were grown in a greenhouse under long-day nursery conditions (18 hr light at 80° F. then 6 hr dark at 74° F.) for approximately four weeks. At eleven weeks, the R0 plants were sprayed with two passes of the same herbicide solution (0.3 g of S-3100) described above. Herbicide injury ratings were collected seven days after treatment.

The results of the herbicide tolerance application at eleven weeks to the R0 plants confirmed the low percent injury rating scores observed in the high-throughput screen at five weeks. Any injury rating of 30% or above was equivalent to non-transgenic soybean injury ratings. A few of the constructs stood out as providing very good tolerance to the herbicide application. For example, TP1 with PPO H_N90 (SEQ ID NO:11) had only 3% injury and with PPO H_N30 (SEQ ID NO:14) or PPO H_N40 (SEQ ID NO:15) had only 5% injury; TP20 with PPO H_N90 (SEQ ID NO:11) had only 5% injury. In contrast, TP32 with the PPO H_N90 (SEQ ID NO:11) had an injury score of 50%. Data are provided in Table 10, where n.d. indicates the analysis was not conducted.

TABLE 10

R0 transgenic soybean herbicide tolerance: percent injury scores

| Targeting Peptide | H_N20 | H_N30 | H_N40 | H_N50 | H_N90 | H_N100 |
|---|---|---|---|---|---|---|
| TP1 | n.d. | 5 | 5 | n.d. | 3 | 15 |
| TP2 | n.d. | n.d. | n.d. | n.d. | 35 | n.d. |
| TP3 | n.d. | n.d. | n.d. | n.d. | 30 | n.d. |
| TP4 | n.d. | n.d. | 15 | n.d. | n.d. | n.d. |
| TP5 | n.d. | n.d. | n.d. | n.d. | n.d. | n.d. |
| TP6 | 25 | n.d. | n.d. | 40 | 25 | 30 |
| TP7 | 20 | n.d. | 40 | n.d. | 15 | 30 |
| TP8 | n.d. | n.d. | 30 | n.d. | 40 | n.d. |
| TP9 | n.d. | 35 | n.d. | 40 | 30 | n.d. |
| TP10 | n.d. | n.d. | n.d. | n.d. | 30 | 35 |
| TP11 | n.d. | 35 | n.d. | n.d. | 30 | n.d. |
| TP12 | 20 | n.d. | n.d. | n.d. | 30 | 50 |
| TP13 | 20 | n.d. | 15 | 40 | 15 | n.d. |
| TP14 | n.d. | n.d. | 35 | 40 | 25 | n.d. |
| TP15 | 30 | 35 | 30 | 40 | 35 | 30 |
| TP16 | n.d. | n.d. | n.d. | n.d. | 35 | n.d. |
| TP17 | 25 | n.d. | n.d. | 40 | 15 | n.d. |
| TP18 | n.d. | n.d. | n.d. | n.d. | 30 | n.d. |
| TP19 | n.d. | n.d. | n.d. | n.d. | n.d. | n.d. |
| TP20 | 20 | n.d. | n.d. | n.d. | 5 | 35 |
| TP21 | n.d. | n.d. | 35 | n.d. | 25 | n.d. |
| TP22 | n.d. | n.d. | n.d. | n.d. | 40 | 30 |
| TP23 | n.d. | n.d. | n.d. | n.d. | 30 | 35 |
| TP24 | n.d. | n.d. | n.d. | n.d. | n.d. | n.d. |
| TP25 | n.d. | n.d. | 15 | 35 | n.d. | n.d. |
| TP26 | n.d. | 35 | n.d. | n.d. | 40 | n.d. |
| TP27 | n.d. | n.d. | n.d. | n.d. | 35 | n.d. |
| TP28 | n.d. | n.d. | n.d. | n.d. | 30 | 35 |
| TP29 | 30 | n.d. | n.d. | n.d. | n.d. | 40 |
| TP30 | n.d. | n.d. | n.d. | n.d. | n.d. | n.d. |
| TP31 | n.d. | n.d. | n.d. | n.d. | n.d. | n.d. |
| TP32 | n.d. | n.d. | n.d. | n.d. | 50 | 40 |
| TP33 | n.d. | n.d. | n.d. | n.d. | 25 | n.d. |
| TP34 | n.d. | n.d. | n.d. | n.d. | 35 | n.d. |
| TP35 | n.d. | n.d. | n.d. | n.d. | 15 | 35 |

TABLE 10-continued

R0 transgenic soybean herbicide tolerance: percent injury scores

| Targeting Peptide | H_N20 | H_N30 | H_N40 | H_N50 | H_N90 | H_N100 |
|---|---|---|---|---|---|---|
| TP36 | n.d. | n.d. | n.d. | n.d. | 15 | n.d. |
| TP37 | n.d. | n.d. | n.d. | n.d. | n.d. | n.d. |

To further evaluate the plant transformation constructs in soybean, excised embryos (A3555) are transformed using plant transformation vectors with *A. tumefaciens* and standard methods known in the art. Regenerated R0 transgenic plantlets are grown in the green house and split into groups. The groups are sprayed with one or more PPO herbicides per group to evaluate herbicide tolerance. For example, the R0 transgenic plants are sprayed at approximately V2-V4 growth stage with lactofen at a rate of 110 g ai/ha (0.09 lb ai/acre) or 220 g ai/ha (0.19 lb ai/acre). Plants are evaluated for injury one to fourteen days after treatment and injury scores are recorded. Leaf samples are used to identify transgenic plants with a single copy of the transgenic DNA insert, and R0 plants that contain only a single copy and pass herbicide spray testing are selfed to produce R1 seed.

R1 plants are grown in the green house and split into groups. The groups are sprayed with one or more PPO herbicides per group to evaluate herbicide tolerance. For example, the PPO herbicide lactofen is applied pre-emergent and/or at the V2 to V6 growth stage at a rate of 220 g ai/ha (0.19 lb ai/acre). Plants are evaluated for injury one to fourteen days after treatment and injury scores are recorded. Unsprayed transgenic plants are used for phenotypic comparison with unsprayed wild-type plants.

R2 plants are generated by selfing a homozygous transgenic R1 plant and collecting seed. R2 plants are evaluated at one or more field locations or greenhouse assays. Herbicide treatments are applied and plots or plants are rated for crop injury one to fourteen days after herbicide application on a scale of 0-100 with zero being no injury and 100 being complete crop death.

Example 7: Leaf Disc Assay

A leaf-disc assay was employed for rapid and minimally damaging assessment of herbicide tolerance in transgenic plants expressing a recombinant PPO enzyme. Leaf tissue was sampled from the youngest fully-green leaf of corn and soybean plants. Five 4-mm diameter leaf discs were cut from the leaf samples using a disposable biopsy punch with a plunger (Integra® Miltex®, Inc., York, Pa.) and the leaf discs were placed into one ml of incubation solution (1 mM MES, pH 6.5, 1% w/v sucrose, 1% (v/v) acetone) in 24-well polystyrene plates with lids. For herbicide tolerance analysis, S-3100 was added to the incubation solution to a final concentration of 1 micromolar. Vacuum infiltration was applied and plates of leaf discs were incubated in continuous darkness for one day at room temperature (23-24° C.) followed by one (soybean) or two (corn) days continuous light incubation under overhead fluorescent and incandescent bulbs (520 uE) at 26-27° C. Leaf disc injury was then scored visually on a scale from 0 (lowest injury) to 4 (highest injury), with lower scores indicating better tolerance to the PPO herbicide.

Leaf discs from transgenic maize plants produced using construct 6 and expressing PPO enzyme H_N10 (SEQ ID NO: 4) showed significant herbicide tolerance based upon an average leaf disc score of 0.4. This result was consistent with the PPO herbicide tolerance observed in whole plants transformed with construct 6 and expressing PPO enzyme H_N10 (SEQ ID NO: 4). Leaf discs from transgenic soy plants produced using construct 1 and construct 11 and expressing PPO enzyme H_N10 (SEQ ID NO: 4) showed that plants with construct 1 had significant herbicide tolerance with an injury rating of zero, while plants with construct 11 had an injury rating of 1.6 and non-transgenic plants had an injury rating of 2.6.

Example 8: Expression and Testing of HemG PPO Enzymes in Cotton

The microbial HemG PPO enzymes are expressed in transgenic cotton plants, and the transgenic plants are analyzed for PPO herbicide tolerance. In cotton, excised embryos (Coker 130) are transformed with these vectors using *A. tumefaciens* and standard methods known in the art. Regenerated R0 transgenic plantlets are grown in the green house and split into groups. The groups are used to spray PPO herbicides (one PPO herbicide per group) to evaluate tolerance. For example, the R0 transgenic plantlets are sprayed at approximately 2-4 true leaf growth stage with lactofen at a rate of 110 g ai/ha (0.09 lb ai/acre) or 220 g ai/ha (0.19 lb ai/acre). Plants are evaluated for injury one to fourteen days after treatment and injury scores are recorded. Leaf samples are used to identify transgenic plants with a single copy of the transgenic insert. R0 plants that contain only a single copy and pass herbicide spray testing are selfed to produce R1 seed.

R1 plants are grown in the green house and split into groups. The groups are sprayed with one or more PPO herbicides per group to evaluate herbicide tolerance. For example, the PPO herbicide lactofen is applied pre-emergent and/or at the two true leaf to first flower stage at a rate of 220 g ai/ha (0.19 lb ai/acre) (1×). Plants are evaluated for injury one to fourteen days after treatment and injury scores are recorded. Unsprayed transgenic plants are used for phenotypic comparison with unsprayed wild-type plants.

R2 plants are generated by selfing a homozygous transgenic R1 plant and collecting seed. R2 plants are evaluated at one or more field locations or greenhouse assays. Herbicide treatments are applied and plots or plants are rated for crop injury one to fourteen days after herbicide application on a scale of 0-100 with zero being no injury and 100 being complete crop death.

What is claimed is:

1. A recombinant DNA molecule comprising a heterologous promoter operably linked to a nucleic acid sequence encoding a protein that has at least 90% sequence identity to a polypeptide sequence selected from the group consisting of: SEQ ID NO:6 and SEQ ID NO:15, wherein the protein has herbicide-insensitive protoporphyrinogen oxidase activity, and wherein the heterologous promoter is functional in a plant cell.

2. The recombinant DNA molecule of claim 1, wherein the nucleic acid sequence is selected from the group consisting of SEQ ID NO:37, SEQ ID NO:46, and SEQ ID NO:59.

3. The recombinant DNA molecule of claim 1, wherein the protein comprises an amino acid sequence selected from the group consisting of SEQ ID NO:6 and SEQ ID NO:15.

4. The recombinant DNA molecule of claim 1, wherein the nucleic acid sequence is operably linked to a DNA molecule encoding a targeting sequence that functions to localize the operably linked protein within the plant cell.

5. A DNA construct comprising the recombinant DNA molecule of claim 1.

6. The DNA construct of claim 5, wherein the recombinant DNA comprises an operably linked DNA molecule encoding a targeting sequence that functions to localize the protein within the plant cell.

7. The DNA construct of claim 5, wherein the protein confers herbicide tolerance to said plant cell.

8. The DNA construct of claim 5, wherein the DNA construct is present in the genome of a transgenic plant, seed, or cell.

9. A transgenic plant, seed, cell, or plant part comprising the recombinant DNA molecule of claim 1.

10. The transgenic plant, seed, cell, or plant part of claim 9, wherein the transgenic plant, seed, cell, or plant part comprises an additional transgenic herbicide tolerance trait.

11. The transgenic plant, seed, cell, or plant part of claim 9, defined as comprising herbicide tolerance to at least one PPO herbicide.

12. A seed according to claim 9.

13. A method for conferring herbicide tolerance to a plant, seed, cell, or plant part comprising: heterologously expressing in said plant, seed, cell, or plant part the recombinant DNA molecule of claim 1.

14. The method of claim 13, wherein the herbicide tolerance is to at least one PPO herbicide selected from the group consisting of: acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil and S-3100.

15. A method of plant transformation, comprising the steps of:
  a) introducing the recombinant DNA molecule of claim 1 into a plant cell; and
  b) regenerating a plant therefrom that comprises the recombinant DNA molecule.

16. The method of claim 15, further comprising the step of selecting a plant that is tolerant to at least one PPO herbicide.

17. The method of claim 15, further comprising the step of crossing the regenerated plant with itself or with a second plant and collecting seed from the cross.

18. A method for controlling weeds in a plant growth area, comprising contacting a plant growth area comprising the transgenic plant or seed of claim 9 with at least one PPO herbicide, wherein the transgenic plant or seed is tolerant to the PPO herbicide and wherein weeds are controlled in the plant growth area.

19. A method of producing a plant tolerant to a PPO herbicide and at least one other herbicide comprising:
  a) obtaining a plant according to claim 9; and
  b) crossing the transgenic plant with a second plant comprising tolerance to the at least one other herbicide, and
  c) selecting a progeny plant resulting from said crossing that comprises tolerance to a PPO herbicide and the at least one other herbicide.

20. A method for reducing the development of herbicide tolerant weeds comprising:
  a) cultivating in a crop growing environment a plant according to claim 10; and
  b) applying a PPO herbicide and at least one other herbicide to the crop growing environment, wherein the crop plant is tolerant to the PPO herbicide and the at least one other herbicide.

21. The method of claim 20, wherein the PPO herbicide is selected from the group consisting of acifluorfen, fomesafen, lactofen, fluoroglycofen-ethyl, oxyfluorfen, flumioxazin, azafenidin, carfentrazone-ethyl, sulfentrazone, fluthiacet-methyl, oxadiargyl, oxadiazon, pyraflufen-ethyl, saflufenacil and S-3100.

22. The method of claim 20, wherein the at least one other herbicide is selected from the group consisting of: an ACCase inhibitor, an ALS inhibitor, an EPSPS inhibitor, a synthetic auxin, a photosynthesis inhibitor, a glutamine synthesis inhibitor, a HPPD inhibitor, a PPO inhibitor, and a long-chain fatty acid inhibitor.

23. The method of claim 22, wherein the ACCase inhibitor is an aryloxyphenoxy propionate or a cyclohexanedione; the ALS inhibitor is a sulfonylurea, imidazolinone, triazoloyrimidine, or a triazolinone; the EPSPS inhibitor is glyphosate; the synthetic auxin is a phenoxy herbicide, a benzoic acid, a carboxylic acid, or a semicarbazone; the photosynthesis inhibitor is a triazine, a triazinone, a nitrile, a benzothiadiazole, or a urea; the glutamine synthesis inhibitor is glufosinate; the HPPD inhibitor is an isoxazole, a pyrazolone, or a triketone; the PPO inhibitor is a diphenylether, a N-phenylphthalimide, an aryl triazinone, or a pyrimidinedione; or the long-chain fatty acid inhibitor is a chloroacetamide, an oxyacetamide, or a pyrazole.

24. The recombinant DNA molecule of claim 1, wherein the protein has at least 95% sequence identity to a polypeptide sequence selected from the group consisting of: SEQ ID NO:6 and SEQ ID NO:15.

25. A transgenic plant, seed, cell, or plant part comprising the recombinant DNA molecule of claim 24.

\* \* \* \* \*